(12) United States Patent
Onishi et al.

(10) Patent No.: US 8,457,905 B2
(45) Date of Patent: Jun. 4, 2013

(54) SOOT DISCHARGE ESTIMATING DEVICE FOR INTERNAL COMBUSTION ENGINES

(75) Inventors: Tomomi Onishi, Susono (JP); Shigeki Nakayama, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 272 days.

(21) Appl. No.: 12/812,406

(22) PCT Filed: May 18, 2009

(86) PCT No.: PCT/JP2009/059474
§ 371 (c)(1),
(2), (4) Date: Jul. 9, 2010

(87) PCT Pub. No.: WO2009/139507
PCT Pub. Date: Nov. 19, 2009

(65) Prior Publication Data
US 2010/0286930 A1 Nov. 11, 2010

(30) Foreign Application Priority Data
May 16, 2008 (JP) ................................ 2008-129039

(51) Int. Cl.
*G01N 31/00* (2006.01)
*G01F 25/00* (2006.01)
(52) U.S. Cl.
USPC ............................................ 702/24; 702/100
(58) Field of Classification Search
USPC .................................................. 702/24, 100
See application file for complete search history.

(56) References Cited

U.S. PATENT DOCUMENTS

| 7,930,922 B2 * | 4/2011 | Onishi et al. ................. 73/23.31 |
| 2003/0149536 A1 * | 8/2003 | Silvis et al. ..................... 702/24 |
| 2006/0179826 A1 | 8/2006 | Kuboshima et al. |
| 2008/0022972 A1 | 1/2008 | Shimo et al. |
| 2012/0143472 A1 * | 6/2012 | Onishi .......................... 701/102 |

FOREIGN PATENT DOCUMENTS

| DE | 10 2006 000 036 A1 | 8/2006 |
| FR | 2 882 093 A1 | 8/2006 |
| JP | A-11-148412 | 6/1999 |
| JP | A-2001-207830 | 8/2001 |

(Continued)

OTHER PUBLICATIONS

International Search Report in International Application No. PCT/JP2009/059474; dated Aug. 18, 2009.

(Continued)

*Primary Examiner* — Michael Nghiem
(74) *Attorney, Agent, or Firm* — Oliff & Berridge, PLC

(57) ABSTRACT

A soot discharge amount is calculated by multiplying a "steady discharge amount" by a "transient correction value." The steady discharge amount is a soot discharge amount in a steady operation state, and is acquired through table search. For each of a plurality of factors which affect the soot discharge amount, a steady value (value obtained through table search) of the factor and a transient value (current value) of the factor are substituted for a characteristic equation which represents a change in the soot discharge amount with the value of the factor, whereby a steady characteristic value and a transient characteristic value are acquired. The "ratio between the steady characteristic value and the transient characteristic value" is then calculated for each factor. The transient correction value is obtained by multiplying together all values of the "ratio between the steady characteristic value and the transient characteristic value" obtained for the factors.

8 Claims, 30 Drawing Sheets

FOREIGN PATENT DOCUMENTS

| | | |
|---|---|---|
| JP | A-2003-286879 | 10/2003 |
| JP | A-2003-307110 | 10/2003 |
| JP | A-2004-132328 | 4/2004 |
| JP | A-2004-183581 | 7/2004 |
| JP | A-2004-204821 | 7/2004 |
| JP | A-2005-048743 | 2/2005 |
| JP | A-2006-046299 | 2/2006 |
| JP | A-2006-226119 | 8/2006 |
| JP | A-2006-316682 | 11/2006 |
| JP | A-2007-023959 | 2/2007 |
| JP | A-2007-046477 | 2/2007 |
| JP | A-2008-031874 | 2/2008 |
| JP | A-2008-057486 | 3/2008 |

OTHER PUBLICATIONS

International Preliminary Report on Patentability in International Application No. PCT/JP2009/059474; dated Jan. 11, 2011.

Aug. 1, 2012 Office Action issued in connection with the corresponding Japanese Application No. 2010-512045(with translation).

* cited by examiner

| | | |
|---|---|---|
| FUEL MIST |  |  |
| Roxc | HIGH | LOW |
| IGNITION DELAY | SMALL | LARGE |
| COMBUSTION PERIOD | SHORT | LONG |

| | | |
|---|---|---|
| FUEL MIST |  |  |
| IGNITION DELAY PERIOD | SHORT | LONG |
| MIST AVERAGE $\phi$ | LARGE | SMALL |
| SOOT DISCHARGE AMOUNT | LARGE | SMALL |

SOOT DISCHARGE ESTIMATING DEVICE FOR INTERNAL COMBUSTION ENGINES

TECHNICAL FIELD

The present invention relates to a soot discharge estimating device for estimating the discharge amount of soot (fine particles of carbon) generated in a combustion chamber of an internal combustion engine as a result of reaction of fuel.

BACKGROUND ART

Soot is the main component of particulate matter (PM) generated in a combustion chamber of an internal combustion engine (particularly, a diesel engine). In order to accurately control the discharge amount of such soot to thereby reduce the same, the discharge amount of soot must be accurately estimated.

For example, a soot discharge estimating device for an internal combustion engine disclosed in Japanese Patent Application Laid-Open (kokai) No. 2007-46477 employs a method for accurately estimating the discharge amount of soot, even when the internal combustion engine is in a transient operation state, through use of a complex reaction model based on the mechanism of generation of soot.

DISCLOSURE OF THE INVENTION

In the apparatus described in the publication, since a complex reaction model is used for estimation of the discharge amount of soot, calculation load associated with estimation of the soot discharge amount is considerably large. Therefore, there has been desire for a method of accurately estimating the discharge amount of soot, even when the internal combustion engine is in a transient operation state, while reducing the calculation load.

The present invention has been accomplished so as to solve the above-described problem, and its object is to provide a soot discharge estimating device for an internal combustion engine which can accurately estimate the discharge amount of soot, with a small calculation load, even when the internal combustion engine is in a transient operation state.

A soot discharge estimating device according to the present invention comprise steady discharge amount acquisition means, steady value acquisition means, transient value acquisition means, transient correction value calculation means, and soot discharge amount estimations. In the following, these means will be described successively.

The steady discharge amount acquisition means acquires a steady discharge amount of soot on the basis of a previously stored relation (table, map) between discharge amount of soot discharged from the internal combustion engine and at least operation speed and fuel injection amount of the internal combustion engine in the case where the internal combustion engine is in a steady operation state, and respective current values of the operation speed and the fuel injection amount. The "steady discharge amount" is a discharge amount of soot in the case where the internal combustion engine is operated in a steady operation state at the current operation speed and with the current fuel injection amount. This "relation" can be acquired in advance through an experiment or the like.

The steady value acquisition means acquires a steady value of a factor that affects the discharge amount of soot on the basis of a previously stored relation (table, map) between the value of a predetermined parameter that represents an operation state of the internal combustion engine and the value of the factor in the case where the internal combustion engine is in the steady operation state, and a current value of the predetermined parameter.

The "factor that affects the discharge amount of soot" is, for example, the temperature, pressure, oxygen concentration, etc. of gas within a combustion chamber. The "predetermined parameter" is, for example, the operation speed, fuel injection amount, etc. of the internal combustion engine. The "steady value of the factor" is a value of the factor in the case where the internal combustion engine is operated in a steady operation state with the current parameter value (for example, the current operation speed and the current fuel injection amount). This "relation" can also be acquired in advance through an experiment or the like.

The transient value acquisition means acquires a transient value of the factor, which is a current value of the factor. This "transient value of the factor" is, for example, a value detected or estimated by means for detecting or estimating the current value of the factor.

The transient correction value calculation means calculates a transient correction value regarding the discharge amount of soot from a steady characteristic value and a transient characteristic value, the steady characteristic value being obtained on the basis of the steady value of the factor and a previously stored characteristic that represents a change in the discharge amount of soot with the value of the factor, and the transient characteristic value being obtained on the basis of the transient value of the factor and the characteristic. In the case where multiple factors are present, for each factor, the above-mentioned characteristic is set, and the steady characteristic value and the transient characteristic value are calculated, respectively.

The "transient correction value" is, for example, the difference, ratio, etc. between the steady characteristic value and the transient characteristic value. In the case where multiple factors are present, the transient correction value is the sum, product, or the like of the difference, ratio, etc. between the steady characteristic value and the transient characteristic value for each factor. In a transient operation state, the transient value of the factor may deviate from the steady value thereof. The transient correction value serves as a value which represents the degree of deviation of the soot discharge amount from the steady discharge amount attributable to the "deviation of the transient value of the factor from the steady value of the factor," which may arise in the transient operation state.

The soot discharge amount estimation means estimates the discharge amount of soot on the basis of the steady discharge amount and the transient correction value. The discharge amount of soot can be obtained, for example, by means of multiplying the steady discharge amount by the transient correction value, or adding the transient correction value to the steady discharge amount. In the steady operation state, the transient correction value is calculated to become "1" (in the case where the steady discharge amount is multiplied by the transient correction value), or calculated to become "0" (in the case where the transient correction value is added to the steady discharge amount). Therefore, the discharge amount of soot coincides with the steady discharge amount.

According to the above-described configuration, the discharge amount of soot can be estimated accurately even in a transient operation state through processing that requires a small calculation load; i.e., table search for acquiring the steady discharge amount and calculation of the transient correction value.

In the soot discharge estimating device according to the present invention, the factor may be a factor that affects the soot generation speed, which is the speed at which soot is generated as a result of reaction of fuel and/or a factor that affects the soot oxidation speed, which is the speed at which the generated soot is oxidized. This is based on the fact that the generation speed (discharge speed) of soot is represented by the difference between the soot generation speed and the soot oxidation speed.

Examples of the factor that affects the soot generation speed include the temperature, pressure, etc. of gas within the combustion chamber. Another example of the factor that affects the soot generation speed is the oxygen concentration of gas within the combustion chamber. The reason why the oxygen concentration of gas within the combustion chamber can be used as the factor that affects the soot generation speed is that, when the oxygen concentration is low, the combustion speed of fuel decreases, and the combustion period of fuel (accordingly, a period of time over which fuel is exposed to high temperature) increases, whereby soot is readily produced. Meanwhile, examples of the factor that affects the soot oxidation speed include the temperature, oxygen concentration, etc. of gas within the combustion chamber.

Other examples of the factor that affects the soot generation speed include an ignition delay period (a period between a point in time at which fuel injection starts and a point in time at which ignition of injected fuel starts), and a value correlated with the ignition delay period. The reason why the ignition delay period can be used as the factor that affects the soot generation speed is that, when the ignition delay period is short, the size of fuel mist at the ignition start time becomes small, and the (average) equivalence ratio of fuel mist increases, whereby soot is readily produced.

Compression end temperature (the temperature of gas within the combustion chamber of the internal combustion engine at the compression top dead center) can be used as the ignition delay period correlated value. This is because, when the compression end temperature is high, the ignition start time becomes earlier, and the ignition delay period becomes shorter. That is, when the compression end temperature is high, soot is readily produced.

Furthermore, the pressure of gas within an exhaust passage of the internal combustion engine (exhaust gas pressure) can be used as the ignition delay period correlated value. This is because, when the exhaust gas pressure is high, the amount of internal EGR gas (exhaust gas circulated from the exhaust passage to the combustion chamber via an exhaust value of the internal combustion engine) increases, and the compression end temperature increases (accordingly, the ignition delay period becomes shorter). That is, when the exhaust gas pressure is high, soot is readily produced.

Furthermore, the temperature of gas within the exhaust passage of the internal combustion engine (exhaust gas temperature) can be used as the ignition delay period correlated value. This is because, when the exhaust gas temperature is high, the temperature of the internal EGR gas increases, and the compression end temperature increases (accordingly, the ignition delay period becomes shorter). That is, when the exhaust gas temperature is high, soot is readily produced.

Furthermore, the temperature of gas within an intake passage of the internal combustion engine (intake gas temperature) can be used as the ignition delay period correlated value. This is because, when the intake gas temperature is high, the compression end temperature increases (accordingly, the ignition delay period becomes shorter). That is, when the intake gas temperature is high, soot is readily produced.

Furthermore, a value obtained in consideration of both the exhaust gas temperature and the intake gas temperature can be used as the ignition delay period correlated value. Specifically, there can be used a value obtained from the exhaust gas temperature, the intake gas temperature, and an internal EGR ratio. The internal EGR ratio is the ratio of the amount of the internal EGR gas to the sum of the amount of the internal EGR gas and the amount of external EGR gas (exhaust gas circulated from the exhaust passage to the combustion chamber of the internal combustion engine via an exhaust gas circulation passage connecting the exhaust passage and the intake passage together).

The degree of influence of the exhaust gas temperature on the compression end temperature (accordingly, on the ignition delay period) greatly depends on the internal EGR ratio. In other words, the degree of influence of the intake gas temperature on the compression end temperature (accordingly, on the ignition delay period) greatly depends on the value of (1-internal EGR ratio). The above-described configuration is based on this finding. By virtue of the above-described configuration, the ignition delay period correlated value can be calculated in consideration of the degrees of influence of the exhaust gas temperature and the intake gas temperature on the compression end temperature (accordingly, on the ignition delay period). Since the transient correction value is calculated to assume a more proper value, the discharge amount of soot can be estimated more accurately in a transient operation state.

In the following, additional explanation is provided for the case where the above-mentioned ignition delay period or the above-mentioned ignition delay period correlated value is used as the factor that affects the soot generation speed. In this case, preferably, only when a predetermined condition is satisfied, the transient correction value is calculated in consideration of the ignition delay period, which serves the factor that affects the soot generation speed, or the value correlated with the ignition delay period; and, when the predetermined condition is not satisfied, the transient correction value is calculated without consideration of the ignition delay period or the value correlated with the ignition delay period. With this configuration, the transient correction value is calculated without consideration of the ignition delay period under the condition that the ignition delay period readily becomes stable or the condition that the degree of influence of the length of the ignition delay period on the degree of generation of soot is small (that is, when the predetermined condition is not satisfied). Thus, when the transient correction value is calculated under such a condition, without lowering calculation accuracy, an increase in calculation load, which would otherwise occur as a result of taking the ignition delay period into consideration, can be avoided.

Specifically, the predetermined condition is satisfied when the oxygen concentration of gas within the combustion chamber of the internal combustion engine or a value correlated with the oxygen concentration is less than a predetermined value. This is because, when the oxygen concentration of gas within the combustion chamber is high, soot is less likely to be produced, and the degree of influence of the length of the ignition delay period on the degree of generation of soot is small.

Furthermore, the predetermined condition is satisfied when pilot injection is not performed prior to main injection. This is because, when pilot injection is performed prior to main injection, the compression end temperature becomes stable irrespective of the exhaust gas pressure, and, therefore, the ignition delay period readily becomes stable.

Furthermore, the predetermined condition is satisfied when the temperature of the wall of the combustion chamber is higher than a predetermined value. This is because, when the temperature of the wall of the combustion chamber is low, the compression end temperature hardly increases even if the exhaust gas pressure, etc. increase, so that the compression end temperature becomes stable, and, therefore, the ignition delay period readily becomes stable.

Furthermore, the predetermined condition is satisfied when the flame temperature within the combustion chamber in an expansion stroke falls within a predetermined range. This is because, when the flame temperature falls outside the predetermined range, generation of soot is less likely to occur, and the degree of influence of the length of the ignition delay period on the degree of generation of soot is small. Notably, the flame temperature refers to the maximum value of the flame temperature (maximum flame temperature) or the like.

Furthermore, in the case where, as described above, the transient correction value is calculated in consideration of the ignition delay period only when the predetermined condition is satisfied, the transient correction value may be calculated in consideration of the ignition delay period (or the value correlated with the ignition delay period) only when the transient value of the ignition delay period (or the value correlated with the ignition delay period) has deviated from the steady value thereof in such a direction that the discharge amount of soot increases. In this case, the transient correction value is calculated without consideration of the ignition delay period "when the transient value of the ignition delay period has deviated from the steady value thereof in such a direction that the discharge amount of soot decreases," which hardly raises a problem associated with the discharge amount of soot. With this operation, in such a case, when the transient correction value is calculated, it is possible to avoid an increase in calculation load, which would otherwise occur as a result of taking the ignition delay period into consideration.

In the soot discharge estimating device according to the present invention, in the case where at least one of the temperature and oxygen concentration of gas within the combustion chamber of the internal combustion engine is used as the factor that affects the soot oxidation speed, the transient correction value calculation means may be configured to calculate the transient correction value on the basis of the steady characteristic value and the transient characteristic value regarding at least one of the temperature and oxygen concentration of the gas in the first half of combustion of fuel, and the steady characteristic value and the transient characteristic value regarding at least one of the temperature and oxygen concentration of the gas in the second half of combustion of fuel.

Oxidation of the generated soot occurs not only in the first half of combustion of fuel (an intermediate stage in which fuel mist is dispersing; a high-temperature mist state in which combustion continues), but also in the second half of combustion of fuel (a state in which the fuel mist has sufficiently dispersed, the gas mixture has become uniform, and the combustion has almost ended). Since the temperature and oxygen concentration of gas within the combustion chamber change greatly between the first half of combustion and the second half of combustion, the oxidation speed (degree of oxidation) of soot also changes greatly between the first half of combustion and the second half of combustion. Accordingly, conceivably, oxidation of soot in the first half of combustion and that in the second half of combustion are desirably handled separately. The above-described configuration is based on this finding.

In this case, preferably, a ratio between the degree of oxidation of soot in the first half of combustion and that in the second half of combustion is determined on the basis of at least one of the temperature, pressure, and oxygen concentration of gas within the combustion chamber, and transient correction value is calculated in consideration of the ratio.

The reason whey the "ratio" can be determined on the basis of at least one of the temperature, pressure, and oxygen concentration of gas within the combustion chamber will be described in detail later. With this configuration, in the case where the above-mentioned factor is a factor that affects the soot oxidation speed, the transient correction value serves a value that more accurately represents the degree of deviation of the soot discharge amount from the steady discharge amount attributable to "deviation of the transient value of the factor from the steady value of the factor."

Furthermore, preferably, as the factor that affects the soot oxidation speed, there can be used the net oxygen concentration of gas within the combustion chamber which contributes to oxidation of soot, the net oxygen concentration being obtained in consideration of a combustion gas intake ratio, which is a ratio of the amount of gas within the combustion chamber required for complete combustion of all fuel of the fuel injection amount to the entire amount of gas within the combustion chamber of the internal combustion engine.

The amount of gas within the combustion chamber required for complete combustion of all fuel of the fuel injection amount can be calculated on the basis of the fuel injection amount and the oxygen concentration of gas within the combustion chamber, and the amount of gas increases as the oxygen concentration decreases. Accordingly, the "combustion gas intake ratio" (<1) increases as the oxygen concentration decreases. Specifically, the "net oxygen concentration" is a value obtained by multiplying the oxygen concentration of gas before combustion (approximately equal to the intake gas oxygen concentration) by (1-combustion gas intake ratio).

Oxidation of soot is greatly affected by the oxygen concentration of gas within the combustion chamber. The "combustion gas intake ratio" represents a probability at which fuel mist takes in gas (combustion gas) present after complete combustion in an assumed case where all fuel of the fuel injection amount completely combusts. No oxygen is present within the combustion gas. Accordingly, when oxidation of soot within fuel mist in such a case is considered, the oxygen concentration of gas taken in fuel mist can be said to be approximately equal to the "net oxygen concentration." As a result, the "net oxygen concentration" can serve as a factor that affects the soot discharge amount more strongly than does the oxygen concentration of gas before undergoing combustion (approximately equal to the intake gas oxygen concentration). The above-described configuration is based on this finding.

Furthermore, preferably, as the factor that affects the soot oxidation speed, there is used a mist overlapping degree, which is a ratio of the amount of gas within the combustion chamber required for complete combustion of all fuel of the fuel injection amount, to the amount of gas within the combustion chamber of the internal combustion engine, excluding a portion of the gas that does not contribute to combustion of the fuel.

The gas within the combustion chamber of the internal combustion engine inevitably contains a portion that fuel mist does not reach (which does not mix with fuel mist). This portion corresponds to the "portion that does not contribute to combustion of fuel." When the ratio of a portion of the gas within the combustion chamber which contributes to combustion of fuel to the entire gas is referred as an "air utilization factor," the amount of gas within the combustion chamber, excluding a portion of the gas that does not contribute to combustion of the fuel, can be obtained by multiplying the entire amount of gas within the combustion chamber by the air utilization factor. As in the case of the "combustion gas intake ratio," the mist overlapping degree "increases as the oxygen concentration decreases. As a result of taking the above-mentioned "portion that does not contribute to combustion of fuel" into consideration, the "mist overlapping degree" may exceed "1" in some cases.

The greater the "mist overlapping degree" (in particular, when the mist overlapping degree is greater than "1"), the higher the probability at which fuel mists injected from a plurality of injection holes overlap with one another. In regions where the fuel mists overlap with one another, it becomes difficult for oxygen within the gas to be taken in the fuel mists, whereby the degree of oxidation of soot decreases in these regions. Accordingly, the "mist overlapping degree" can serve as the factor that strongly affects the soot discharge amount. The above-described configuration is based on this finding.

BEST MODE FOR CARRYING OUT THE INVENTION

An embodiment of a soot discharge estimating device for an internal combustion engine (diesel engine) according to the present invention will now be described with reference to the drawings.

Figure 1:
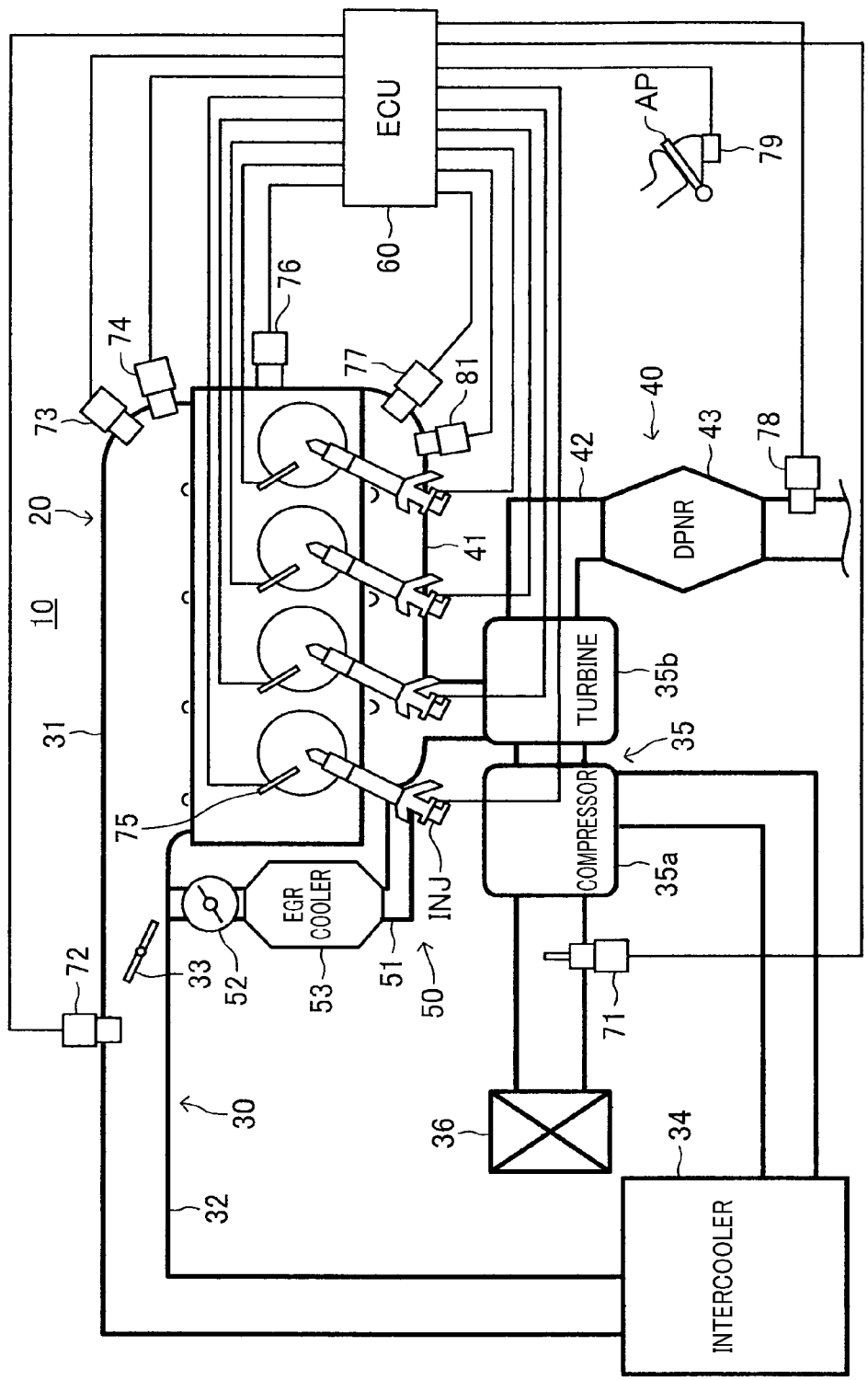
FIG. 1 is a schematic diagram showing the overall configuration of a system in which a soot discharge estimating device for an internal combustion engine according to an embodiment of the present invention is applied to a four-cylinder internal combustion engine (diesel engine).

FIG. 1 schematically shows the entire configuration of a system in which a soot discharge estimating device according to the embodiment of the present invention is applied to a four-cylinder internal combustion engine (diesel engine) 10. This system comprises an engine main body 20 including a fuel supply system; an intake system 30 for introducing gas into combustion chambers (cylinder interiors) of individual cylinders of the engine main body 20; an exhaust system 40 for discharging exhaust gas from the engine main body 20; an EGR apparatus 50 for performing exhaust circulation; and an electronic control apparatus 60.

Fuel injection valves NJ each utilizing a needle are disposed above the individual cylinders of the engine main body 20.

The intake system 30 includes an intake manifold 31, which is connected to the respective combustion chambers of the individual cylinders of the engine main body 20; an intake pipe 32, which is connected to an upstream-side branching portion of the intake manifold 31 and constitutes an intake passage in cooperation with the intake manifold 31; a throttle valve 33, which is rotatably held within the intake pipe 32; an intercooler 34, which is interposed in the intake pipe 32 to be located on the upstream side of the throttle valve 33; a compressor 35a of a turbocharger 35, which is interposed in the intake pipe 32 to be located on the upstream side of the intercooler 34; and an air cleaner 36, which is disposed at a distal end portion of the intake pipe 32.

The exhaust system 40 includes an exhaust manifold 41, which is connected to the individual cylinders of the engine main body 20; an exhaust pipe 42, which is connected to a downstream-side merging portion of the exhaust manifold 41; a turbine 35b of the turbocharger 35 interposed in the exhaust pipe 42; and a diesel particulate filter (DPNR) 43, which is interposed in the exhaust pipe 42. The exhaust manifold 41 and the exhaust pipe 42 constitute an exhaust passage.

The EGR apparatus 50 includes an exhaust circulation pipe 51, which forms a passage (EGR passage) for circulation of exhaust gas; an EGR control valve 52, which is interposed in the exhaust circulation pipe 51; and an EGR cooler 53. The exhaust circulation pipe 51 establishes communication between an exhaust passage (the exhaust manifold 41) located on the upstream side of the turbine 35b, and an intake passage (the intake manifold 31) located on the downstream side of the throttle valve 33. The EGR control valve 52 responds to a drive signal from the electronic control apparatus 60 so as to change the amount of exhaust gas to be circulated (exhaust-gas circulation amount, EGR-gas flow rate).

The electronic control apparatus 60 is a microcomputer which includes a CPU, ROM, RAM, backup RAM, an interface, etc., which are connected to one another by means of a bus. The ROM stores a program to be executed by the CPU, tables (maps), constants, etc. The interface contains A/D converters.

The interface is connected to a hot-wire-type air flow meter 71, an intake gas temperature sensor 72, an intake pipe pressure sensor 73, an intake gas oxygen concentration sensor 74, an in-cylinder pressure sensor 75, an engine speed sensor 76, an exhaust gas temperature sensor 77, an air-fuel-ratio sensor 78, an accelerator opening sensor 79, and an exhaust gas pressure sensor 81. The interface receives respective signals from these sensors, and supplies the received signals to the CPU.

Further, the interface is connected to the fuel injection valves INJ, an unillustrated throttle valve actuator, and the EGR control valve 52; and outputs corresponding drive signals to these components in accordance with instructions from the CPU.

The hot-wire-type air flow meter 71 measures the mass flow rate of intake air passing through the intake passage (intake air quantity per unit time, new air quantity per unit time). The intake gas temperature sensor 72 detects the temperature of gas that is taken into the combustion chambers (cylinders) of the engine 10 (intake gas temperature). The intake pipe pressure sensor 73 detects the pressure of gas that is taken into the combustion chambers of the engine 10 (intake gas pressure). The intake gas oxygen concentration sensor 74 detects the oxygen concentration of gas that is taken into the combustion chambers of the engine 10 (intake gas oxygen concentration).

The in-cylinder pressure sensor 75 detects the pressure of gas within each combustion chamber (in-cylinder pressure). The engine speed sensor 76 detects the actual crank angle and an engine speed; i.e., the rotational speed of the engine 10. The exhaust gas temperature sensor 77 detects the temperature of gas discharged from the combustion chambers (exhaust gas temperature). The air-fuel-ratio sensor 78 detects the air-fuel ratio of exhaust gas downstream of the DPNR 43. The accelerator opening sensor 79 detects an amount by which an accelerator pedal AP is operated (accelerator opening). The exhaust gas pressure sensor 81 detects the pressure of gas discharged from the combustion chambers (exhaust gas pressure).

Soot Discharge Amount Estimation Method According to a First Embodiment

Next, a soot discharge amount estimation method according to a first embodiment of the soot discharge estimating device configured as described above will be described.

Figure 2:
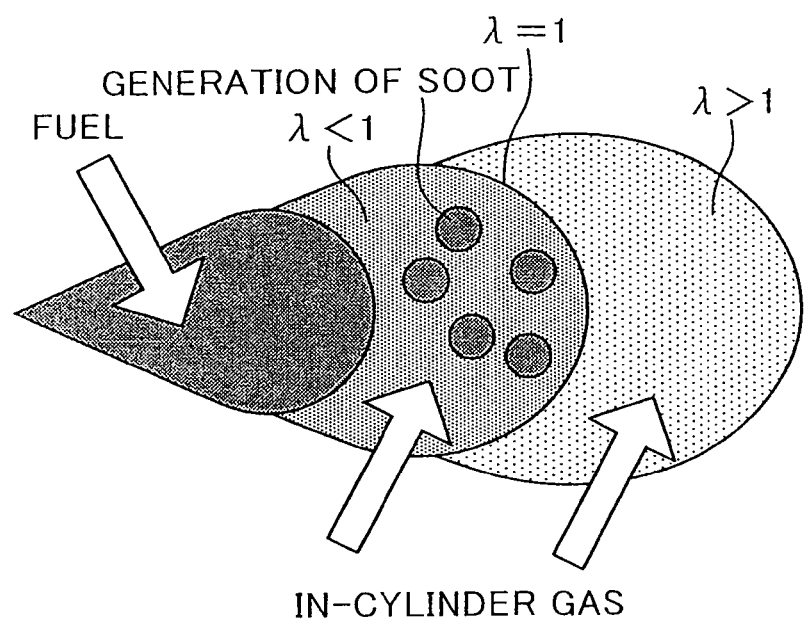
FIG. 2 is a schematic diagram showing a state in which generation of soot mainly occurs in a region of fuel mist in which the excess air ratio is less than 1.
Figure 3:
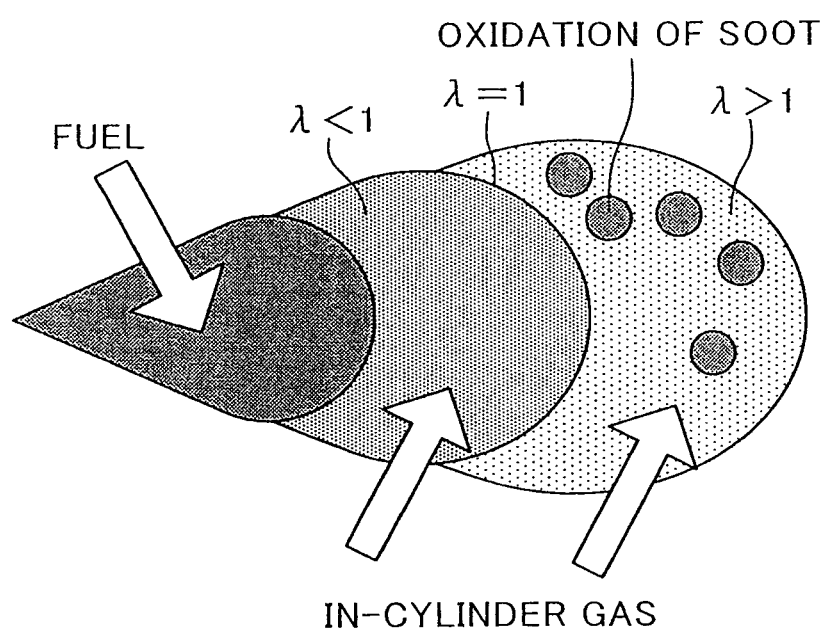
FIG. 3 is a schematic diagram showing a state in which oxidation of soot mainly occurs in a region of fuel mist in which the excess air ratio is greater than 1.

Within in each combustion chamber, soot is generated as a result of reaction of fuel. As shown in FIG. 2, generation of soot takes place mainly in a region of fuel mist in which the excess air ratio λ is less than 1 (especially, in a high temperature region where λ<0.5 and the temperature is equal to or higher than about 1500K). Meanwhile, a portion of the generated soot is oxidized. As shown in FIG. 3, oxidation of the generated soot takes place mainly in a region of fuel mist in which the excess air ratio λ is greater than 1 (especially, in a high temperature region where the temperature is equal to or higher than about 1500K). A portion of the generated soot which is not oxidized is discharged from the combustion chamber as soot. In the first embodiment, the amount of soot discharged from the combustion chamber in this manner (soot discharge amount) is estimated.

In the first embodiment, the "mass of soot discharged from the combustion chambers per unit time" is calculated as the soot discharge amount. That is, the unit of the soot discharge amount calculated in the first embodiment is, for example, g/h or g/s.

In the first embodiment, the soot discharge amount is estimated in accordance with the following Eq. (1). In Eq. (1), the "steady discharge amount" represents a soot discharge amount in the case where the internal combustion engine 10 is operated in a steady operation state at the current operation speed and with the current fuel injection amount. The "transient correction value" is a value (coefficient) which represents the degree of deviation of a soot discharge amount in a transient operation state from the "steady discharge amount." Accordingly, as indicated in Eq. (1), the soot discharge amount in the transient operation state can be calculated by means of multiplying the "steady discharge amount" by the "transient correction value." Estimation of the soot discharge amount by Eq. (1) is executed, for example, every time a timing at which the fuel injection amount is determined comes in the course of a compression stroke of a cylinder into which fuel is injected.

$$\text{Soot discharge amount} = (\text{steady discharge amount}) \cdot (\text{transient correction value}) \quad (1)$$

Figure 4:
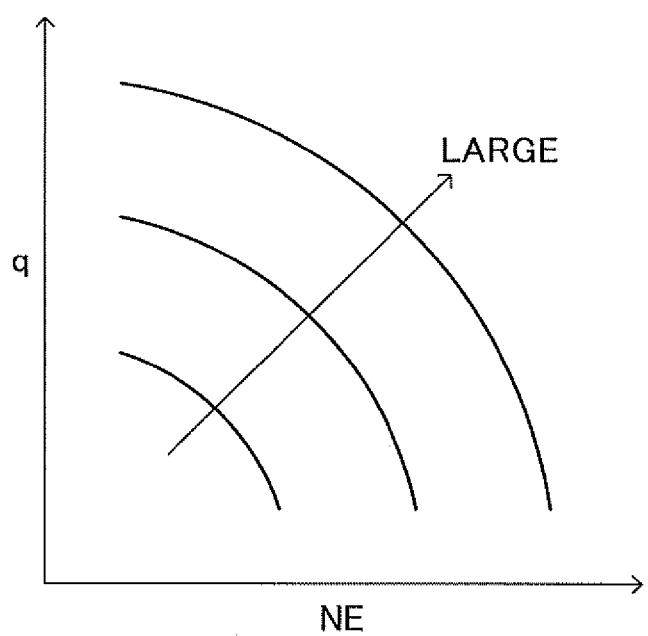
FIG. 4 is a graph showing a table for obtaining a steady discharge amount.

The steady discharge amount is acquired through table search from a table shown in FIG. 4, the current value (instantaneous value) of the engine speed NE, and the current value (value at this time) of the fuel injection amount q. The table is adapted to obtain the steady discharge amount while using the engine speed NE and the fuel injection amount q as arguments. This table can be created by repeating an experiment of measuring the soot discharge amount in a steady operation state in which the engine speed and the fuel injection amount are maintained constant, for each of combinations of different values of the engine speed and the fuel injection amount. As shown in FIG. 4, in general, the steady discharge amount is determined such that the greater the engine speed NE and the greater the fuel injection amount q, the greater the steady discharge amount.

First, the outline of a method of calculating the transient correction value will be described. The transient correction value is calculated from the following Eq. (2). As shown in Eq. (2), in the first embodiment, the transient correction value is calculated from the product of a correction term (correction coefficient) regarding the generation of soot, a correction term (correction coefficient) regarding the oxidation of soot, and a correction term (correction coefficient) regarding mixing of fuel mist and gas within the combustion chamber (in-cylinder gas).

$$\text{Transient correction value} = \underbrace{\frac{A1t}{A1s} \cdot \frac{A2t}{A2s}}_{\text{Generation correction}} \cdot \underbrace{\frac{B1s}{B1t} \cdot \frac{B2s}{B2t}}_{\text{Oxidation correction}} \cdot \underbrace{\frac{C1t}{C1s}}_{\text{Mixing correction}} \quad (2)$$

For calculation of the transient correction value, a plurality of factors (fuel mist representative temperature Tf, in-cylinder pressure Pc, etc. to be described later) that affect the soot discharge amount are introduced. In the following description, in order to facilitate explanation, the factors are collectively referred to as "factor X." Furthermore, for each factor, there is introduced a characteristic equation which represents a change in the soot discharge amount with the value of the factor X (e.g., for the case of Tf, see the graph shown in FIG. 6, which will be described later).

For each factor, a steady value Xs of the factor X and a transient value Xt of the factor X are acquired. The steady value Xs is a value of the factor X when the internal combustion engine 10 is operated in a steady operation state at the current operation speed and with the current fuel injection amount. For each factor, the steady value Xs is obtained, through table search, from a table for obtaining the value of the factor X, the current value (instantaneous value) of the engine speed NE, and the current value (value at this time) of the fuel injection amount q. The table is adapted to obtain the value of the factor X while using the engine speed NE and the fuel injection amount q as arguments, as in the case of the above-described "steady discharge amount." The table for obtaining the value of the factor X can be created by repeating an experiment of measuring the value of the factor X in a steady operation state in which the engine speed and the fuel injection amount are maintained constant, for each of combinations of different values of the engine speed and the fuel injection amount. In the following description, a table which is created in advance for each factor so as to obtain the steady value Xs will be referred to as MapXs (NE, q).

The transient value Xt is the current value (instantaneous value) of the factor X. As will be described later, for each factor, the transient value Xt is obtained from the result of detection by a relevant sensor, the result of estimation performed through use of a known estimation model, etc. In the steady operation state, the transient value Xt coincides with the steady value Xs. In the transient operation state, the transient value Xt may deviate from the steady value Xs. That is, even for the same combination of the current value (instantaneous value) of the engine speed NE and the current value (value at this time) of the fuel injection amount q, the transient value Xt may deviate from the steady value Xs. Due to this deviation, the soot discharge amount deviates from a steady-state fit value.

For each factor, a steady characteristic value regarding the factor X (for example, in the case of Tf, A1s in Eq. (2)) is obtained from the steady value Xs and the above-described "characteristic equation" for the factor X; and a transient characteristic value regarding the factor X (for example, in the case of Tf, A1t in Eq. (2)) is obtained from the transient value Xt and the above-described "characteristic equation" for the factor X. The steady characteristic value and the transient characteristic value are each represented by a variable (A1, etc.) which represents the corresponding characteristic value and which is suffixed with "s" or "t."

For each factor, a ratio between the steady characteristic value and the transient characteristic value is calculated (for example, in the case of Tf, "A1t/A1s" in Eq. (2)). The "ratio between the steady characteristic value and the transient characteristic value" for the factor X serves as a value which represents the degree of deviation of the soot discharge amount from the steady discharge amount attributable to the "deviation of the transient value Xt from the steady value Xs" which may arise in the transient operation state.

As shown in Eq. (2), the transient correction value is calculated by means of multiplying together the values of the "ratio between the steady characteristic value and the transient characteristic value" obtained for the respective factors. As a result, the transient correction value is calculated as a "value (coefficient) representing the degree of deviation of the soot discharge amount from the steady discharge amount" in consideration of all the influence of the "deviation of the transient value Xt from the steady value Xs" for each factor in the transient operation state. Next, for each of the correction terms shown in Eq. (2), the "ratio between the steady characteristic value and the transient characteristic value" for each factor will be described in detail one by one.

<Generation Correction Term>

In a correction term regarding the generation of soot (generation correction term), factors that affect the speed at which soot is generated as a result of reaction of fuel (soot generation speed) are used as the above-described factor. Specifically, fuel mist representative temperature Tf and in-cylinder pressure Pc are introduced as the "factor that affects the soot generation speed." The characteristic values A1 and A2 in Eq. (2) correspond to the fuel mist representative temperature Tf and the in-cylinder pressure Pc, respectively. The factors will be described on a factor-by-factor basis.

<<A1t/A1s Based on Fuel Mist Representative Temperature Tf>>

Figure 5:
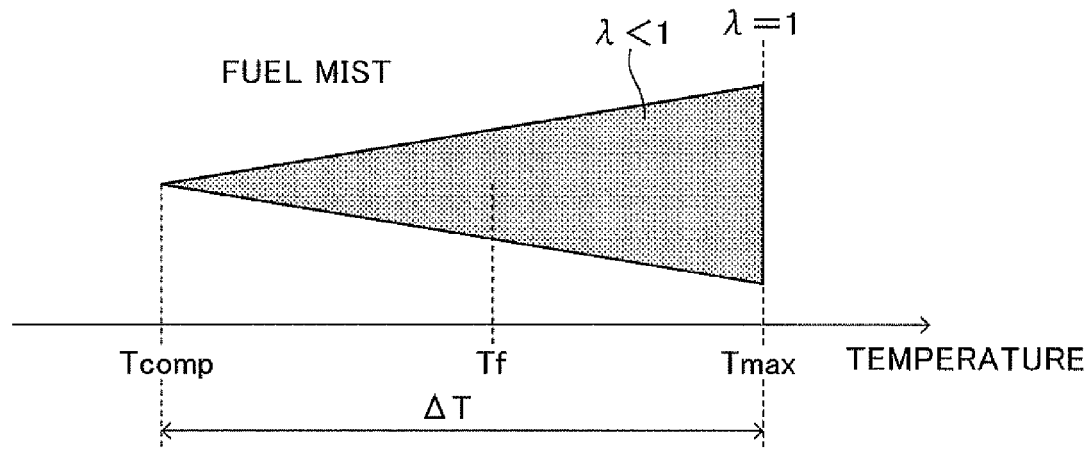
FIG. 5 is a schematic diagram showing a temperature distribution within fuel mist.

The fuel mist representative temperature Tf is a temperature which represents different temperatures at different positions within fuel mist (in particular, in a region in which the excess air ratio is less than 1 and soot is generated). As shown in FIG. 5, in the region of fuel mist injected from an injection hole in which λ<1, a temperature distribution is produced such that the temperature gradually increases from a compression end temperature Tcomp to a maximum flame temperature Tmax as the distance from the injection hole (the root of mist; λ=0) increases (i.e., as the excess air ratio λ increases from 0 to 1).

In the present example, an average temperature, which is the average of the compression end temperature Tcomp and the maximum flame temperature Tmax, a centroid temperature, which is a temperature obtained by weighting the temperature corresponding to each value of λ by the amount of mist (gas mixture) distributing as a function of λ, or the like can be employed as the fuel mist representative temperature Tf.

As described above, the steady value Tfs of the fuel mist representative temperature Tf is obtained, through table search, from a previously created table MapTfs (NE, q), the current value (instantaneous value) of the engine speed NE, and the current value (value at this time) of the fuel injection amount q.

The transient value Tft of the fuel mist representative temperature Tf can be obtained from the current value (value at this time) of the compression end temperature Tcomp and the current value (value at this time) of the maximum flame temperature Tmax. The temperatures Tcomp and Tmax can be obtained, by use of a known method, from intake gas temperature, intake gas pressure, and intake gas oxygen concentration, which can be detected by the above-described sensors; the entire amount of gas taken in the combustion chamber (in-cylinder gas amount); etc. The in-cylinder gas amount can be determined from the intake gas temperature, the intake gas pressure, the volume of the combustion chamber at the start of compression, and an equation of state of gas.

In the present example, a characteristic equation for obtaining a "characteristic value A1 regarding the soot discharge amount" for the fuel mist representative temperature Tf is represented by use of a Gaussian function as shown in the following Eq. (3) and FIG. 6. The reason for the use of the Gaussian function is that the soot generation amount (generation speed) becomes the maximum at a certain temperature Tp (e.g., about 1895K), and decreases as the temperature deviates from Tp.

$$A1 = \exp\left\{-\frac{(Tf - Tp)^2}{2 \cdot \sigma^2}\right\} \quad (3)$$

In the present example, the standard deviation σ (see FIG. 6) used in Eq. (3) can be obtained from the relation that a value obtained by multiplying together "0.68" and half (=ΔT/2) of the difference ΔT (see FIG. 5) between the compression end temperature Tcomp and the maximum flame temperature Tmax is equal to 2σ. The value "0.68" is the "probability at which an observed value of a random variable which follows a Gaussian distribution falls within a range of the average value±(1× the standard deviation)." For example, when ΔT=1200K, σ is approximately 200K.

Figure 6:
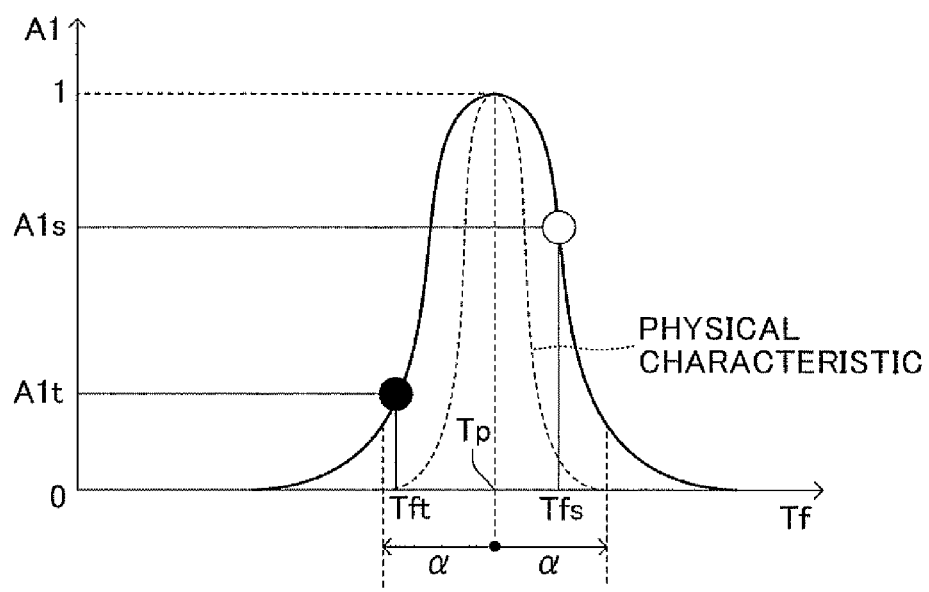
FIG. 6 is a graph showing a change in a "characteristic value A1 regarding the soot discharge amount" with mist representative temperature Tf.

A solid line of FIG. 6 shows an example change in the characteristic value A1 with Tf, which is obtained through use of the standard deviation a determined as described above. Meanwhile, a broken line of FIG. 6 shows a (actual) physical characteristic of the soot discharge amount in a local region (a region where the temperature is uniform) with temperature. This physical characteristic can be obtained through an experiment or the like. As can be understood through comparison between the solid line and the broken line of FIG. 6, the standard deviation σ determined as described above is greater than the standard deviation corresponding to the above-described physical characteristic.

As shown in FIG. 6, the steady characteristic value A1s is obtained from the steady value Tfs and Eq. (3) (that is, through substitution of Tfs for Tf of Eq. (3)) (see a large white circle); and the transient characteristic value A1t is obtained from the transient value Tft and Eq. (3) (that is, through substitution of Tft for Tf of Eq. (3)) (see a large black circle).

Then, "A1t/A1s," which is the "ratio between the steady characteristic value and the transient characteristic value," is calculated (see Eq. (2)). This "A1t/A1s" represents the degree of deviation of the soot discharge amount (instantaneous value) from the steady discharge amount attributable to the "deviation of the transient value Tft from the steady value Tfs" in the transient operation state.

Figure 7:
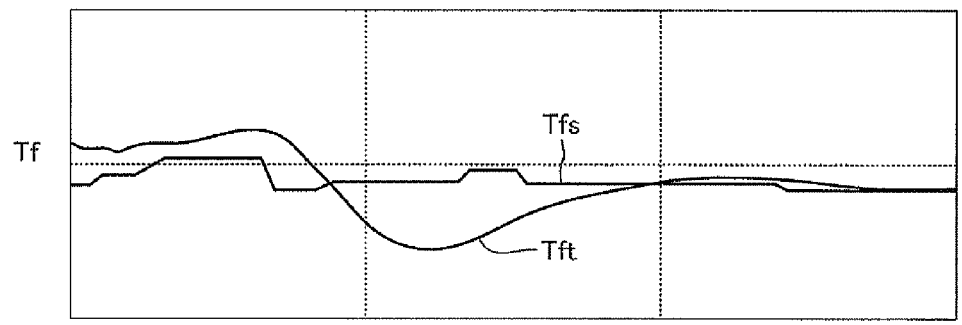
FIG. 7 is a graph showing an example change in the soot discharge amount in the case where steady and transient values Tfs and Tft of mist representative temperature Tf and steady and transient characteristic values A1$s$ and A1$t$ are employed.
Figure 7:
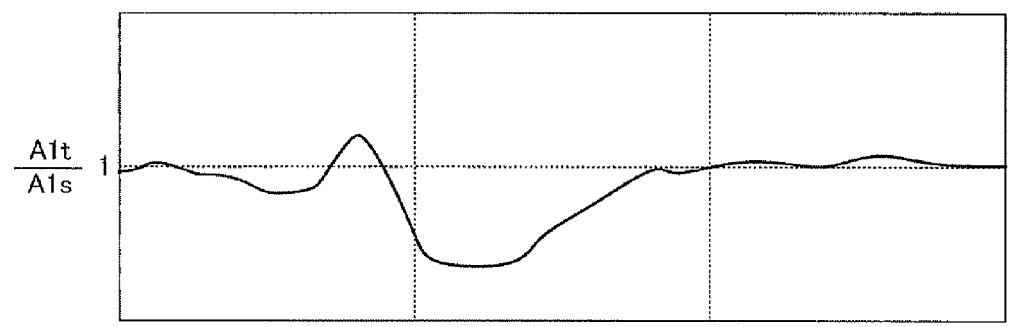
Figure 7:
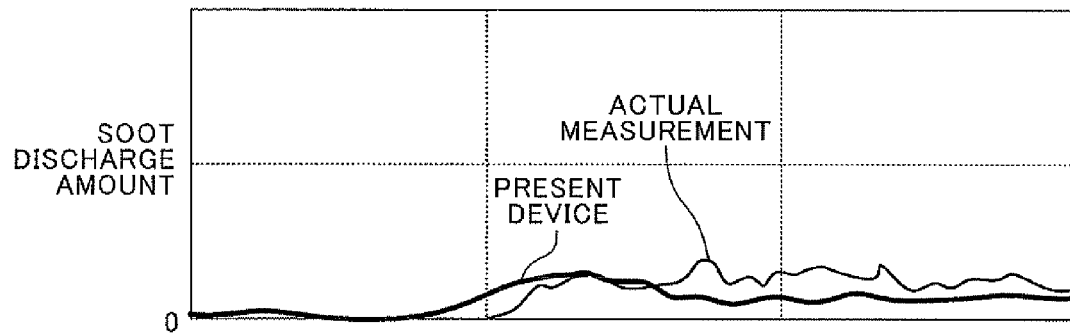

FIG. 7 shows an example (e.g., at the time of sharp acceleration) of changes in Tfs, Tft, A1t/A1s, and the soot discharge amount in the case where Tfs, Tft, A1s, and A1t are set as described above. As shown in FIG. 7, even when Tft greatly deviates from Tfs in a transient operation state, such as at the time of sharp acceleration, by means of multiplying the steady discharge amount by "A1t/A1s," the soot discharge amount can change without greatly deviating from an actually measured value.

As described above, different temperatures at different potions within a region of fuel mist in which the excess air ratio λ is less than 1 are represented by a single temperature Tf, and the standard deviation a used in a characteristic equation (Gaussian function) for obtaining the "characteristic value A1 regarding the soot discharge amount" for Tf is set to a value greater than the standard deviation corresponding to the above-described physical characteristic. Through this procedure, without increasing the calculation load, "A1t/A1s" can be calculated as a value which accurately represents the degree of deviation of the soot discharge amount (instantaneous value) from the steady discharge amount attributable to the "deviation of the transient value Tft from the steady value Tfs" in a transient operation state.

<<A2t/A2s Based on In-Cylinder Pressure Pc>>

The in-cylinder pressure Pc is the pressure within the combustion chamber at a predetermined timing. In the present example, the pressure within the combustion chamber at the time when the intake valve is closed, or the like can be employed as the in-cylinder pressure Pc. Since the pressure within the combustion chamber at the time when the intake valve is closed is considered to be approximately equal to the intake gas pressure, it can be obtained from the intake pipe pressure sensor 73. Alternatively, the compression end pressure may be employed as the in-cylinder pressure Pc. The compression end pressure can be obtained, for example, from the in-cylinder pressure sensor 75.

As described above, the steady value Pcs of the in-cylinder pressure Pc can be obtained, through table search, from the previously created table MapPcs (NE, q), the current value (instantaneous value) of the engine speed NE, and the current value (value at this time) of the fuel injection amount q.

As described above, the transient value Pct of the in-cylinder pressure Pc can be obtained from the intake pipe pressure sensor 73, the in-cylinder pressure sensor 75, etc.

Figure 8:
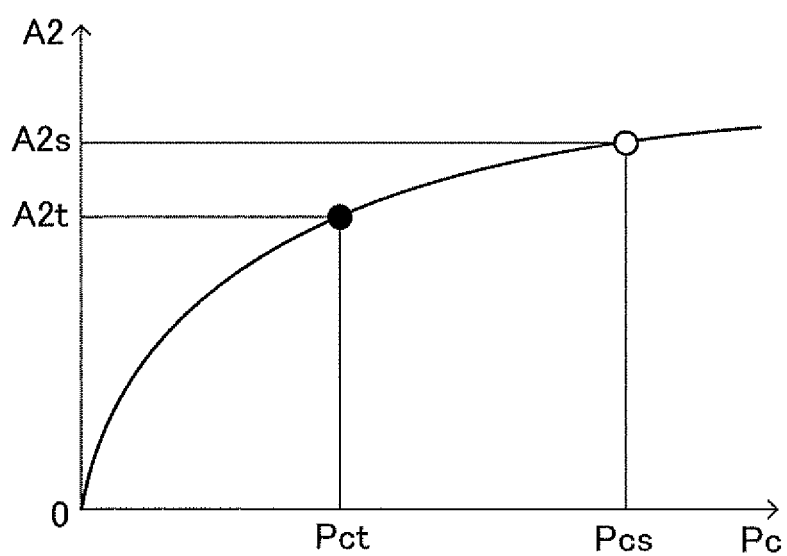
FIG. 8 is a graph showing a change in a "characteristic value A2 regarding the soot discharge amount" with in-cylinder pressure Pc.

In the present example, a characteristic equation for obtaining the "characteristic value A2 regarding the soot discharge amount" for the in-cylinder pressure Pc is represented by the following Eq. (4). FIG. 8 shows a change in the characteristic value A2 with Pc. The reason for employment of Eq. (4) is that the soot generation amount (generation speed) changes in proportion to the square root of the pressure.

$$A2 = \sqrt{Pc} \quad (4)$$

As shown in FIG. 8, the steady characteristic value A2s is obtained from the steady value Pcs and Eq. (4) (that is, through substitution of Pcs for Pc of Eq. (4)) (see a large white circle); and the transient characteristic value A2t is obtained from the transient value Pct and Eq. (4) (that is, through substitution of Pct for Pc of Eq. (4)) (see a large black circle).

Then, "A2t/A2s," which is the "ratio between the steady characteristic value and the transient characteristic value," is calculated (see Eq. (2)). This "A2t/A2s" represents the degree of deviation of the soot discharge amount (instantaneous value) from the steady discharge amount attributable to the "deviation of the transient value Pct from the steady value Pcs" in the transient operation state.

<Oxidation Correction Term>

In a correction term regarding the oxidation of soot (oxidation correction term), factors that affect the speed at which the generated soot is oxidized (soot oxidation speed) are used as the above-described "factor." Specifically, oxidation region representative temperature To1 and in-cylinder oxygen concentration Roxc are introduced as the "factor that affects the soot oxidation speed." The characteristic values B1 and B2 in the above-described Eq. (2) correspond to the oxidation region representative temperature To1 and the in-cylinder oxygen concentration Roxc, respectively. The factors will be described on a factor-by-factor basis.

<<B1s/B1t Based on Oxidation Region Representative Temperature To1>>

The oxidation region representative temperature To1 is a temperature which represents different temperatures at different locations within fuel mist (in particular, within a region in which the excess air ratio λ is greater than 1, and soot is oxidized); in particular, a representative temperature within a region of fuel mist in which the excess air ratio λ is greater than 1 in the first half of combustion of fuel; i.e., an intermediate stage in which fuel mist is dispersing.

Figure 9:
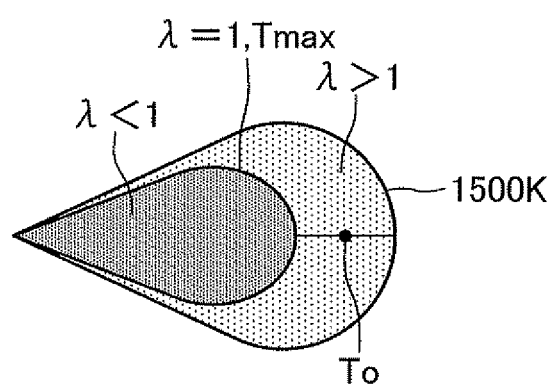
FIG. 9 is a diagram used for explaining calculation of oxidation region representative temperature To1.

As shown in FIG. 9, in a region in fuel mist in which λ>1, a temperature distribution is produced such that the temperature gradually decreases from the maximum flame temperature Tmax with separation from a portion corresponding to the maximum flame temperature Tmax (λ=1) toward the forward end of the mist (that is, as the excess air ratio λ increases from 1). In addition, most soot oxidation reactions occur at temperatures equal to or higher than 1500K.

In view of the above, in the present example, for example, the average between the maximum flame temperature Tmax and 1500K or the like is employed as the oxidation region representative temperature To1 as shown in the following Eq. (5).

$$To1 = (Tmax + 1500)/2 \quad (5)$$

As described above, the steady value To1s of the oxidation region representative temperature To1 is obtained, through table search, from a previously created table MapTo1s (NE, q), the current value (instantaneous value) of the engine speed NE, and the current value (value at this time) of the fuel injection amount q.

The transient value To1t of the oxidation region representative temperature To1 can be obtained from the above-described Eq. (5). As described above, Tmax can be obtained, by use of a known method, from the intake gas temperature, the intake gas pressure, and the intake gas oxygen concentration, which can be detected by the above-described sensors; the above-described in-cylinder gas amount; etc. Notably, Tmax decreases as Roxc decreases.

Figure 10:
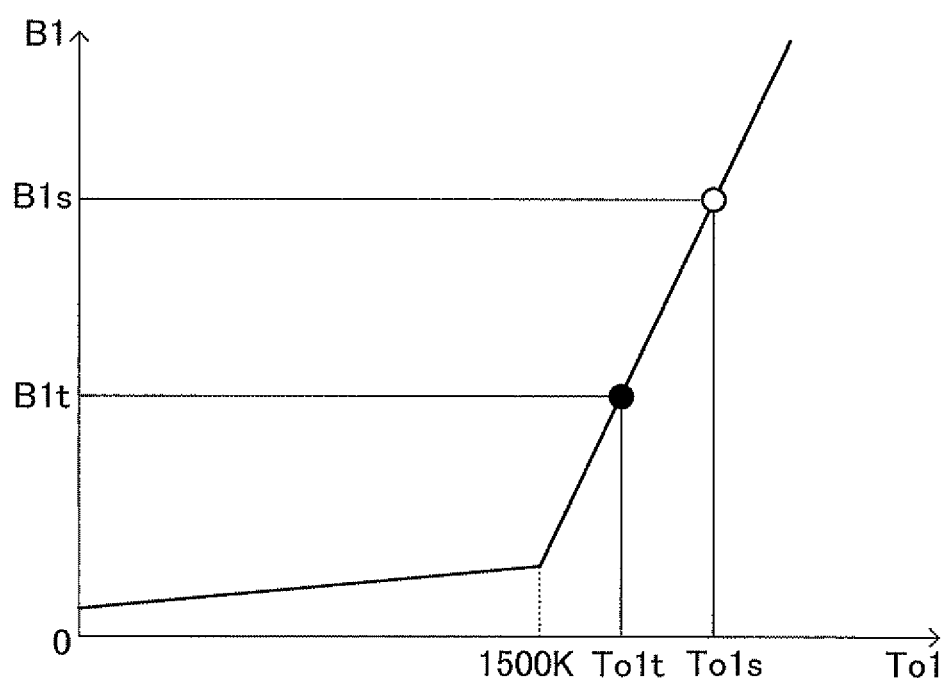
FIG. 10 is a graph showing a change in a "characteristic value B1 regarding the soot discharge amount" with the oxidation region representative temperature To1.

In the present example, a characteristic equation for obtaining the "characteristic value B1 regarding the soot discharge amount" for the oxidation region representative temperature To1 is represented by the following Eq. (6). q1, q2, h1, and h2 are positive constants (q2>q1). FIG. 10 shows a change in the characteristic value B1 with To1. As shown in FIG. 10, the characteristic value B1 is very small when To1 is lower than 1500K, and substantially increases with To1 when To1 becomes equal to or higher than 1500K. The reason for employment of such a characteristic is that, as described above, most of soot oxidation reactions occur at temperatures equal to or higher than 1500K, and the soot oxidation reaction speed increases with temperature when the temperature is equal to or higher than 1500K.

$$B1 = q1 \cdot To1 + h1 \, (To1 \leq 1500K)$$

$$q2 \cdot To1 - h2 \, (To1 > 1500K) \quad (6)$$

As shown in FIG. 10, the steady characteristic value B1s is obtained from the steady value To1s and Eq. (6) (that is, through substitution of To1s for To1 of Eq. (6)) (see a large white circle); and the transient characteristic value B1t is obtained from the transient value To1t and Eq. (6) (that is, through substitution of To1t for To1 of Eq. (6)) (see a large black circle).

Then, "B1t/B1s," which is the "ratio between the steady characteristic value and the transient characteristic value," is calculated (see Eq. (2)). This "B1t/B1s" represents the degree of deviation of the soot discharge amount (instantaneous value) from the steady discharge amount attributable to the "deviation of the transient value To1t from the steady value To1s" in the transient operation state.

Notably, as the oxidation of soot proceeds, the soot discharge amount decreases. Accordingly, in the oxidation correction term, when a characteristic value which increases with the progress of the oxidation of soot is used, in contrast to the above-described generation correction term (="the transient characteristic value/the steady characteristic value"), a fraction "the steady characteristic value/the transient characteristic value" in which the values of the numerator and the denominator are reversed is used as the ratio between the "steady characteristic value and the transient characteristic value."

As described above, different temperatures at different potions within a region of fuel mist in which the excess air ratio λ is greater than 1 (in particular, in the first half of combustion) are represented by a single temperature To1. Through this procedure, without increasing the calculation load, "B1t/B1s" can be calculated as a value which accurately represents the degree of deviation of the soot discharge amount (instantaneous value) from the steady discharge amount attributable to the "deviation of the transient value To1t from the steady value To1s" in a transient operation state.

In addition, it is possible to express that, when the maximum flame temperature Tmax (accordingly, the oxidation region representative temperature To1) decreases as a result of a decrease in the in-cylinder oxygen concentration Roxc, the degree of oxidation of soot decreases (accordingly, the soot discharge amount increases).

<<B2s/B2t Based on In-Cylinder Oxygen Concentration Roxc>>

The in-cylinder oxygen concentration Roxc is the oxygen concentration of gas within the combustion chamber. Since the oxygen concentration of gas within the combustion chamber is considered to be approximately equal to the oxygen concentration of gas taken in the combustion chamber, it can be obtained from the intake gas oxygen concentration sensor 74.

As described above, the steady value Roxcs of the in-cylinder oxygen concentration Roxc is obtained, through table search, from a previously created table MapRoxcs (NE, q), the current value (instantaneous value) of the engine speed NE, and the current value (value at this time) of the fuel injection amount q.

The transient value Roxct of the in-cylinder oxygen concentration Roxc can be obtained from the intake gas oxygen concentration sensor 74 as described above.

Figure 11:
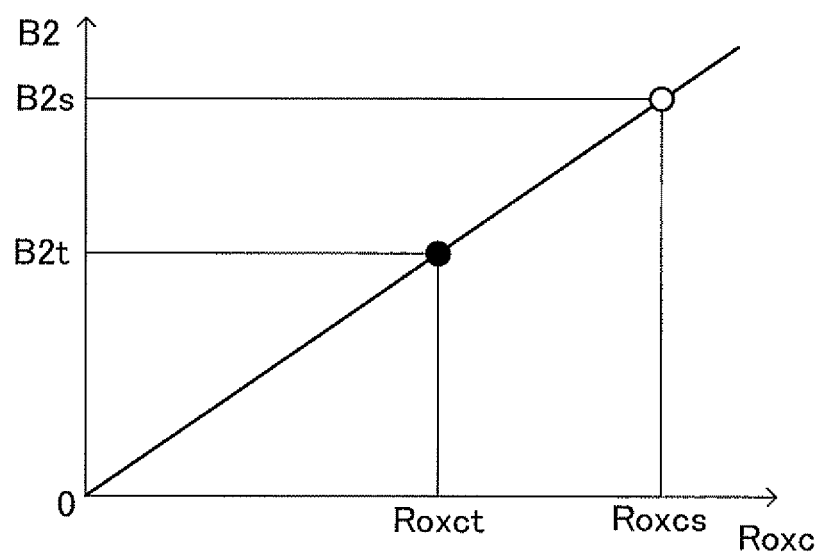
FIG. 11 is a graph showing a change in a "characteristic value B2 regarding the soot discharge amount" with in-cylinder oxygen concentration Roxc.

In the present example, a characteristic equation for obtaining the "characteristic value B2 regarding the soot discharge amount" for the in-cylinder oxygen concentration Roxc is represented by the following Eq. (7). FIG. 11 shows a change in the characteristic value B2 with Roxc. The reason for employment of Eq. (7) is that the soot oxidation speed changes in proportion to the in-cylinder oxygen concentration.

$$B2 = Roxc \quad (7)$$

As shown in FIG. 11, the steady characteristic value B2s is obtained from the steady value Roxcs and Eq. (7) (that is, through substitution of Roxcs for Roxc of Eq. (7)) (see a large white circle); and the transient characteristic value B2t is obtained from the transient value Roxct and Eq. (7) (that is, through substitution of Roxct for Roxc of Eq. (7)) (see a large black circle).

Then, "B2s/B2t," which is the "ratio between the steady characteristic value and the transient characteristic value," is calculated (see Eq. (2)). This "B2s/B2t" accurately represents the degree of deviation of the soot discharge amount (instantaneous value) from the steady discharge amount attributable to the "deviation of the transient value Roxct from the steady value Roxcs" in the transient operation state.

<Mixing Correction Term>

In a correction term regarding the mixing between fuel mist and in-cylinder gas (mixing correction term), a combustion gas intake ratio X (which will be described in detail later) is introduced as the above-described "factor." The characteristic value C1 in the above-described Eq. (2) corresponds to the combustion gas intake ratio X.

<<C1t/C1s Based on Combustion Gas Intake Ratio X>>

When the in-cylinder gas amount required to completely combust all fuel of the fuel injection amount q is represented by Gs, Gs can be represented by the following Eq. (8). In Eq. (8), AFth represents a theoretical air-fuel ratio, and Roxc represents the in-cylinder oxygen concentration.

$$Gs = q \cdot AFth \cdot \frac{23.2}{Roxc} \quad (8)$$

Figure 12:
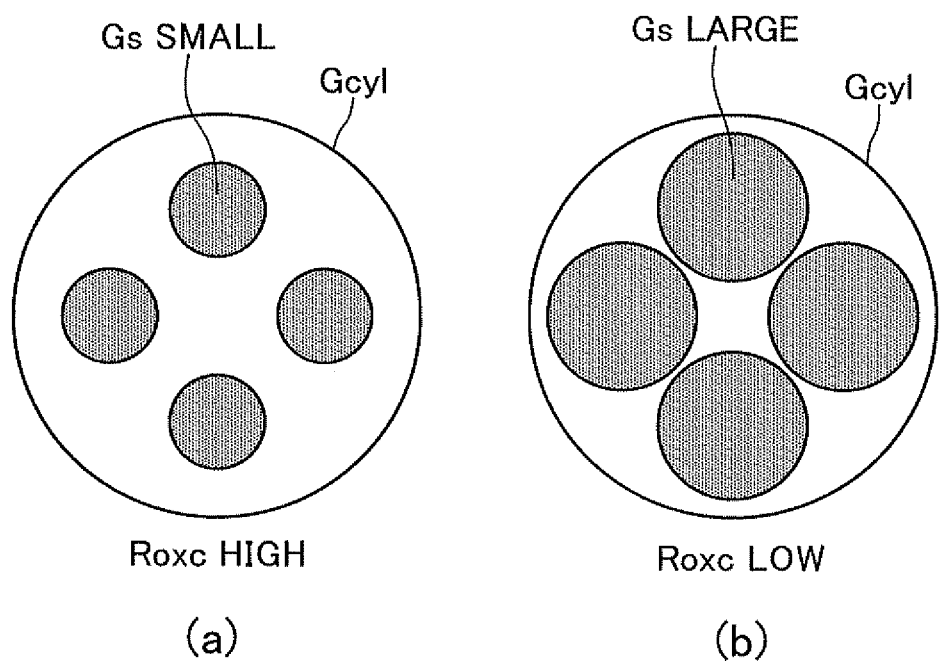
FIG. 12 is a pair of diagrams used for explaining the relation between the in-cylinder oxygen concentration Roxc and an in-cylinder gas amount Gs required for complete combustion of all fuel.

As can be understood from Eq. (8), the smaller the Roxc, the greater the Gs. Accordingly, when the entire amount of in-cylinder gas (=the above-described in-cylinder gas amount) is represented by Gcyl, as shown in FIG. 12, the ratio of Gs to Gcyl decreases when Roxc is large (see FIG. 12(a)), and increases when Ron is small (see FIG. 12(b)).

In an assumed case where all fuel of the fuel injection amount has completely combusted, this ratio (Gs/Gcyl) represents a probability at which fuel mist takes in gas (combustion gas) present after complete combustion. No oxygen is present within the combustion gas. Accordingly, an increase in this ratio (Gs/Gcyl) means that the degree of oxidation of soot generated within fuel mist decreases; that is, the soot discharge amount increases.

Figure 13:
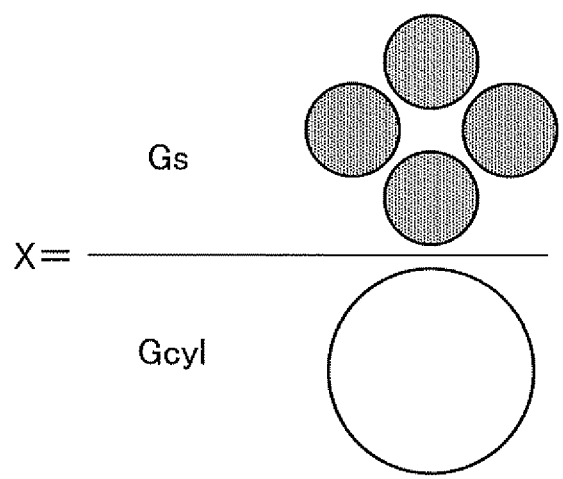
FIG. 13 is a diagram showing an equation which defines a combustion gas intake ratio X.

As described above, the ratio (Gs/Gcyl) is a factor that affects the soot discharge amount. In the present example, as shown in FIG. 13, the ratio (Gs/Gcyl) is defined as a combustion gas intake ratio X (0<X<1).

As described above, the steady value Xs of the combustion gas intake ratio X is obtained, through table search, from a previously created table MapXs (NE, q), the current value (instantaneous value) of the engine speed NE, and the current value (value at this time) of the fuel injection amount q. The transient value Xt of the combustion gas intake ratio X is obtained in accordance with an equation shown in FIG. 13.

Figure 14:
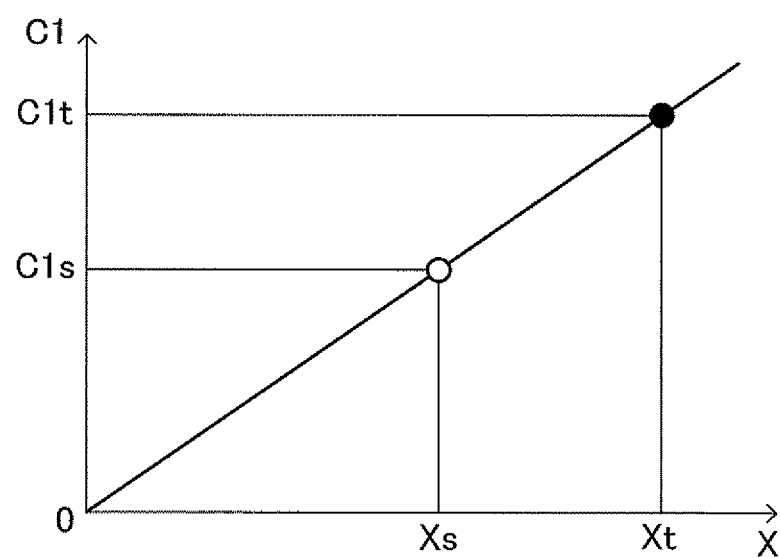
FIG. 14 is a graph showing a change in a "characteristic value C1 regarding the soot discharge amount" with the combustion gas intake ratio X.

In the present example, a characteristic equation for obtaining the "characteristic value C1 regarding the soot discharge amount" for the combustion gas intake ratio X is represented by the following Eq. (9). FIG. 14 represents a change in the characteristic value C1 with X. The reason for employment of Eq. (9) (linear function) is that the soot discharge amount increases with X, and calculation becomes simple.

$$C1 = X \quad (9)$$

As shown in FIG. 14, the steady characteristic value C1s is obtained from the steady value Xs and Eq. (9) (that is, through substitution of Xs for X of Eq. (9)) (see a large white circle); and the transient characteristic value C1t is obtained from the transient value Xt and Eq. (9) (that is, through substitution of Xt for X of Eq. (9)) (see a large black circle).

Then, "C1t/C1s," which is the "ratio between the steady characteristic value and the transient characteristic value," is calculated (see Eq. (2)). This "C1t/C1s" represents the degree of deviation of the soot discharge amount (instantaneous value) from the steady discharge amount attributable to the "deviation of the transient value Xt from the steady value Xs" in the transient operation state.

As described above, through addition of the mixing correction term (=C1t/C1s) to the above-described Eq. (2), it becomes possible to express that the combustion gas intake ratio X (=Gs/Gcyl) increases when oxygen within the cylinder tends to become insufficient transiently (for example, when the in-cylinder gas amount Gcyl is small or when the in-cylinder oxygen concentration Roxc is low), and that, when oxygen within the cylinder tends to become insufficient transiently, the soot discharge amount increases.

As described above, according to the first embodiment of the soot discharge estimating device of the present invention, the soot discharge amount can be calculated by means of multiplying the "steady discharge amount" by the " the transient correction value" (see Eq. (1)). The "steady discharge amount" is a soot discharge amount in the case where the internal combustion engine is operated in a steady operation state at the current operation speed and with the current fuel injection amount, and is obtained through table search. The "transient correction value" is a coefficient that represents the degree of deviation of the soot discharge amount in a transient operation state from the "steady discharge amount." When the "transient correction value" is calculated, for each of a plurality of factors that affect the soot discharge amount, a steady value (value obtained through table search) and a transient value (current value) of each factor are substituted for a corresponding characteristic equation regarding the soot discharge amount for the factor, whereby a steady characteristic value and a transient characteristic value are obtained. The "ratio between the steady characteristic value and the transient characteristic value" is then calculated. The "transient correction value" is calculated from the product of the values of the "ratio between the steady characteristic value and the transient characteristic value" obtained for the respective factors (see Eq. (2)).

Thus, the "transient correction value" is calculated as a "coefficient that represents the degree of deviation of the soot discharge amount from the steady discharge amount" in consideration of all the influence of the "deviation of the transient value from the steady value" for each factor in a transient operation state. As a result, in a transient operation state, the soot discharge amount can be accurately estimated through processing which imposes a small amount of calculation load on the CPU; i.e., table search for acquisition of the "steady discharge amount" and calculation of the "transient correction value."

Soot Discharge Amount Estimation Method According to a Second Embodiment

Next, a soot discharge amount estimation method according to a second embodiment of the soot discharge estimating device of the present invention will be described. This second embodiment differs from the first embodiment only in the point that the transient correction value is calculated from the following Eq. (10), in contrast to the first embodiment in which the transient correction value is calculated from the above-described Eq. (2). In the following, only the difference will be described.

Transient correction value = (10)

$$\underbrace{\frac{A1t}{A1s} \cdot \frac{A2t}{A2s} \cdot \frac{A3t}{A3s}}_{\text{Generation correction}} \cdot \left\{ \alpha \cdot \frac{B1s}{B1t} \cdot \frac{B2's}{B2't} + (1-\alpha) \cdot \underbrace{\frac{B3s}{B3t} \cdot \frac{B4s}{B4t}}_{\text{Oxidation correction}} \right\}$$

As can be understood from Eq. (10), in the second embodiment, the transient correction value is calculated from only the generation correction term and the oxidation correction term. In the generation correction term, as in the first embodiment, the "ratio $A1t/A1s$ based on the fuel mist representative temperature Tf" and the "ratio $A2t/A2s$ based on the in-cylinder pressure Pc are used, but, unlike the first embodiment, a "ratio $A3t/A3s$ based on the in-cylinder oxygen concentration Roxc" is newly introduced.

<<$A3t/A3s$ Based on In-Cylinder Oxygen Concentration Roxc>>

Figure 15:
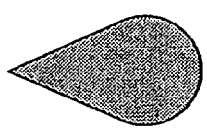
FIG. 15 is an illustration used for explaining the relation among the size of fuel mist, in-cylinder oxygen concentration, ignition delay, and combustion period.
Figure 15:
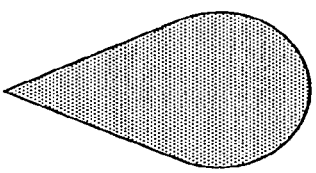

As shown in FIG. 15, when the in-cylinder oxygen concentration Roxc is low, ignition delay increases (a time between fuel injection and ignition increases), and the size of fuel mist at the ignition start time increases. In addition, when the in-cylinder oxygen concentration Roxc is low, the chance for fuel mist to meet oxygen within the in-cylinder gas decreases, and the combustion speed of fuel decreases. Therefore, when the in-cylinder oxygen concentration Roxc is low, the combustion period of fuel increases, and a period of time in which the fuel is exposed to high temperature increases, whereby soot is readily produced.

As described above, the in-cylinder oxygen concentration Roxc is a "factor that affects the soot generation speed." Notably, in consideration of the above-described phenomenon in which, when the in-cylinder oxygen concentration Roxc is low, the size of fuel mist at the ignition start time increases, it can be said that the size of fuel mist at the ignition start time is a "factor that affects the soot generation speed." That is, the greater the size of fuel mist at the ignition start time, the more readily soot is produced.

For example, the size of fuel mist at the ignition start time can be represented by a gas mixture amount Gall which is obtained in accordance with the following Eq. (11). In Eq. (11), there is used the "in-cylinder gas amount Gs required to completely combust all fuel of the fuel injection amount q" (see the above-described Eq. (8)). In calculation of Gs, the in-cylinder oxygen concentration Roxc is used.

$$Gall = q + Gs = q \cdot \left(1 + AFth \cdot \frac{23.2}{Roxc}\right) \quad (11)$$

As described above, the steady value Roxcs of the in-cylinder oxygen concentration Roxc is obtained, through table search, from a previously created table MapRoxcs (NE, q), the current value (instantaneous value) of the engine speed NE, and the current value (value at this time) of the fuel injection amount q. The transient value Roxct of the in-cylinder oxygen concentration Roxc can be obtained from the intake gas oxygen concentration sensor 74 as described above.

Figure 16:
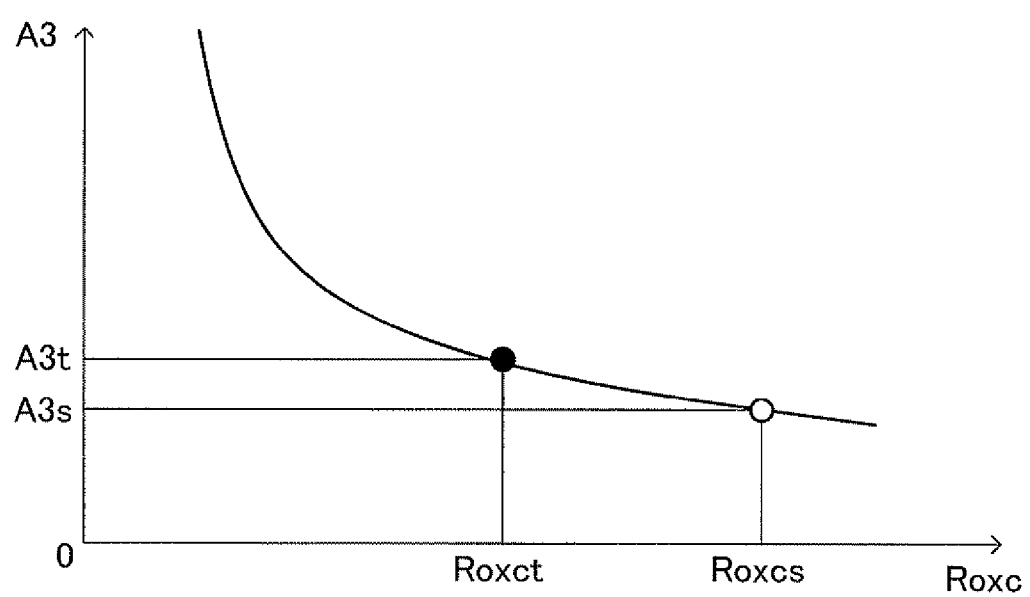
FIG. 16 is a graph showing a change in a "characteristic value A3 regarding the soot discharge amount" with the in-cylinder oxygen concentration Roxc.

In the present example, a characteristic equation for obtaining the "characteristic value A3 regarding the soot discharge amount" for the in-cylinder oxygen concentration Roxc is represented by the following Eq. (12). This characteristic value A3 is a value obtained by means of dividing Gall obtained from Eq. (11) by q. FIG. 16 shows a change in the characteristic value A3 with Roxc. The reason for employment of Eq. (12) is that, as described above, the greater the size of fuel mist at the ignition start time, the greater the easiness of generation of soot and that the size of fuel mist at the ignition start time can be represented by Gall.

$$A3 = 1 + AFth \cdot \frac{23.2}{Roxc} \quad (12)$$

As shown in FIG. 16, the steady characteristic value $A3s$ is obtained from the steady value Roxcs and Eq. (12) (that is, through substitution of Roxcs for Roxc of Eq. (12)) (see a large white circle); and the transient characteristic value $A3t$ is obtained from the transient value Roxct and Eq. (12) (that is, through substitution of Roxct for Roxc of Eq. (12)) (see a large black circle).

Then, "$A3t/A3s$," which is the "ratio between the steady characteristic value and the transient characteristic value," is calculated (see Eq. (10)). This "$A3t/A3s$" represents the degree of deviation of the soot discharge amount (instantaneous value) from the steady discharge amount attributable to the "deviation of the transient value Roxct from the steady value Roxcs" in the transient operation state.

As described above, through addition of "A3t/A3s" to the generation correction term as shown in the above-described Eq. (10), it becomes possible to express that, when the in-cylinder oxygen concentration temporarily decreases (accordingly, the size of fuel mist at the ignition start time increases) at the time of acceleration or the like, soot is more readily produced, and the soot discharge amount increases.

Meanwhile, as can be understood from the above-described Eq. (10), in the second embodiment, the oxidation correction term is identical with that of the first embodiment in that the "ratio B1s/B1t based on the oxidation region representative temperature To1" is used, but differs from that of the first embodiment in that, in place of the "ratio B2s/B2t based on the in-cylinder oxygen concentration Roxc," a "ratio B2's/B2't based on net in-cylinder oxygen concentration Roxc'" is introduced and that a "ratio B3s/B3t based on oxidation region representative temperature To2" and a "ratio B4s/B4t based on in-cylinder oxygen concentration Roxe," and a weighting coefficient α are newly introduced.

Figure 17:
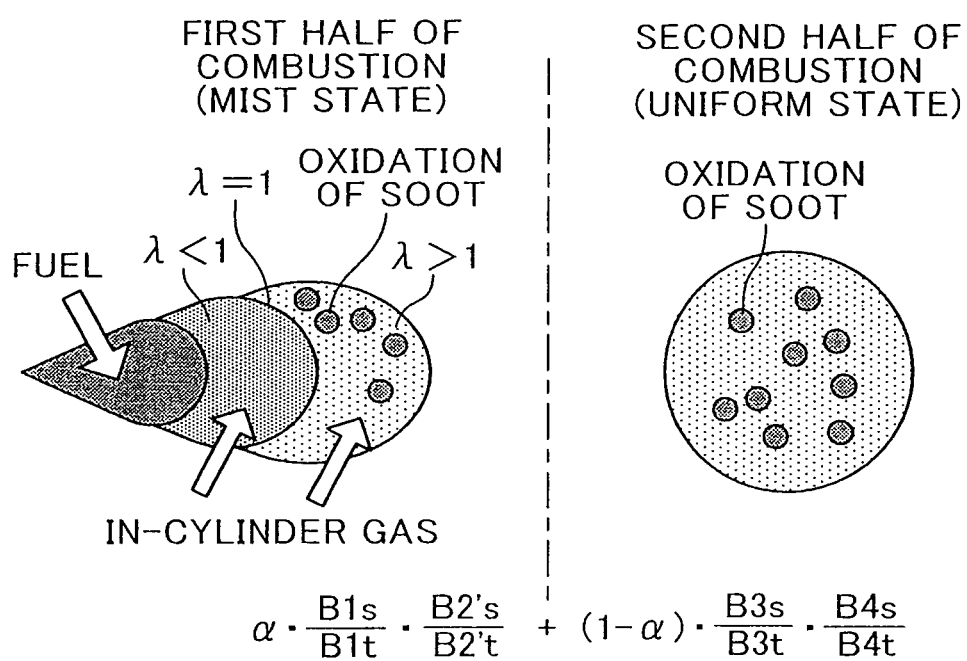
FIG. 17 is an illustration used for explaining a method of calculating an oxidation correction term while separately handling oxidation of soot in the first half of combustion and that in the second half of combustion.

As shown in FIG. 17, oxidation of the generated soot occurs not only in the first half of combustion; i.e., in an intermediate state in which fuel mist is dispersing (a high-temperature mist state in which combustion continues), but also in the second half of combustion; i.e., in a state in which the fuel mist has dispersed sufficiently, the gas mixture has become uniformly, and the combustion has almost ended. Since the temperature and oxygen concentration of gas within the combustion chamber greatly change between the first half of combustion and the second half of combustion, the soot oxidation speed greatly changes therebetween. Accordingly, in the second embodiment, oxidation of soot in the first half of combustion and that in the second half of combustion are handled separately.

As shown in FIG. 17, the "ratio B1s/B1t based on the oxidation region representative temperature To1" and the "ratio B2's/B2't based on the net in-cylinder oxygen concentration Roxc'" relate to the first half of combustion, and the "ratio B3s/B3t based on the oxidation region representative temperature Tot" and the "ratio B4s/B4t based on the in-cylinder oxygen concentration Roxe" relate to the second half of combustion. The weighting coefficient α represents the ratio of the oxidation amount (degree of oxidation) of soot in the first half of combustion to the oxidation amount (degree of oxidation) of soot in the entire combustion. In the following, the items newly introduced in the second embodiment will be described on an item-by-item basis.

<<B2's/B2't based on Net In-Cylinder Oxygen Concentration Roxc'>>

As described above, the combustion gas intake ratio X (=Gs/Gcyl) (see FIG. 13) represents a probability at which fuel mist takes in the combustion gas (gas present after complete combustion) after all fuel of the fuel injection amount is assumed to have combusted completely. No oxygen is present in the combustion gas. Accordingly, when oxidation of soot within the fuel mist after all fuel has combusted completely is considered, the oxygen concentration of gas taken into the fuel mist can be considered to be approximately equal to Roxc' represented by the following Eq. (13).

$$Roxc' = Roxc \cdot (1-X) \qquad (13)$$

Roxc' that is obtained by means of multiplying Roxc (oxygen concentration obtained from the intake gas oxygen concentration sensor 74; in-cylinder oxygen concentration before combustion) by (1−X) as shown in the above-described Eq. (13) will be referred to as a "net in-cylinder oxygen concentration Roxc'." Roxc' determined in consideration of X can serves a factor that affects the soot oxidation speed more strongly than does Roxc.

As described above, the steady value Roxc's of the net in-cylinder oxygen concentration Roxc' is obtained, through table search, from a previously created table MapRoxc's (NE, q), the current value (instantaneous value) of the engine speed NE, and the current value (value at this time) of the fuel injection amount q. The transient value Roxc't of the net in-cylinder oxygen concentration Roxc' is obtained in accordance with the above-described Eq. (13).

Figure 18:
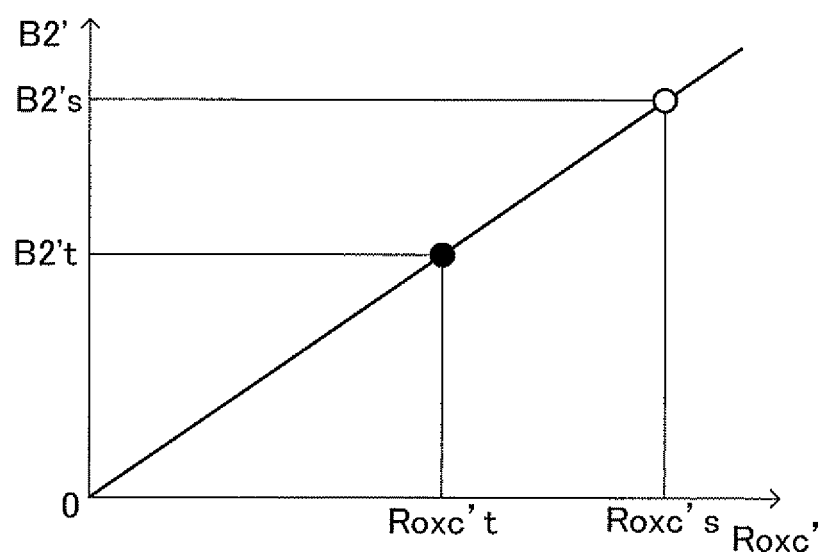
FIG. 18 is a graph showing a change in a "characteristic value B2' regarding the soot discharge amount" with net in-cylinder oxygen concentration Roxc'.

In the present example, a characteristic equation for obtaining the "characteristic value B2' regarding the soot discharge amount" for the net in-cylinder oxygen concentration Roxc' is represented by the following Eq. (14). FIG. 18 shows a change in the characteristic value B2' with Roxc'. The reason for employment of Eq. (14) (linear function) is that the soot oxidation speed in the first half of combustion is in proportion to Roxc'.

$$B2' = Roxc' \qquad (14)$$

As shown in FIG. 18, the steady characteristic value B2's is obtained from the steady value Roxc's and Eq. (14) (that is, through substitution of Roxc's for Roxc' of Eq. (14)) (see a large white circle); and the transient characteristic value B2't is obtained from the transient value Roxc't and Eq. (14) (that is, through substitution of Roxc't for Roxc' of Eq. (14)) (see a large black circle).

Then, "B2's/B2't," which is the "ratio between the steady characteristic value and the transient characteristic value," is calculated (see Eq. (10)). This "B2's/B2't" represents the degree of deviation of the soot discharge amount (instantaneous value) from the steady discharge amount attributable to the "deviation of the transient value Roxc't from the steady value Roxc's" in the transient operation state.

Figure 19:
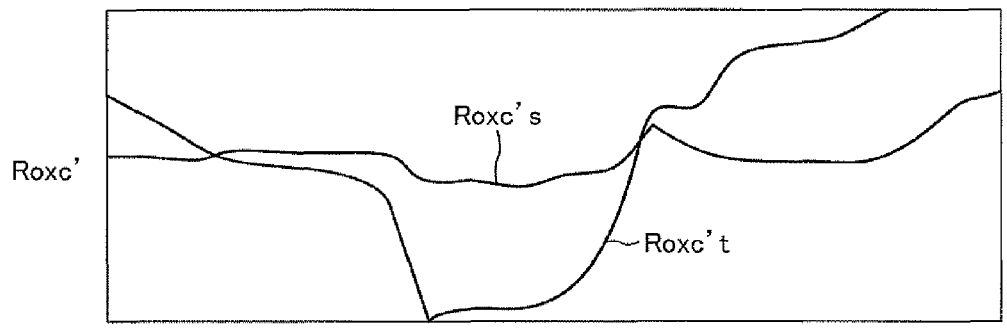
FIG. 19 is a graph showing an example change in the soot discharge amount in the case where steady and transient values Roxc's and Roxc't of the net in-cylinder oxygen concentration Roxc' and steady and transient characteristic values B2'$s$ and B2'$t$ are employed.
Figure 19:
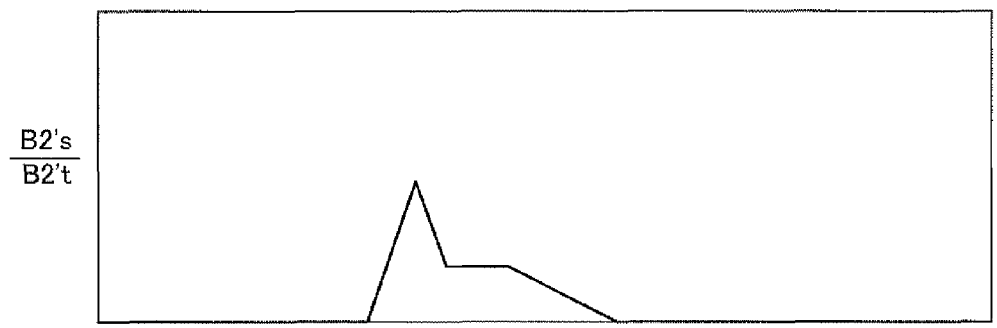
Figure 19:
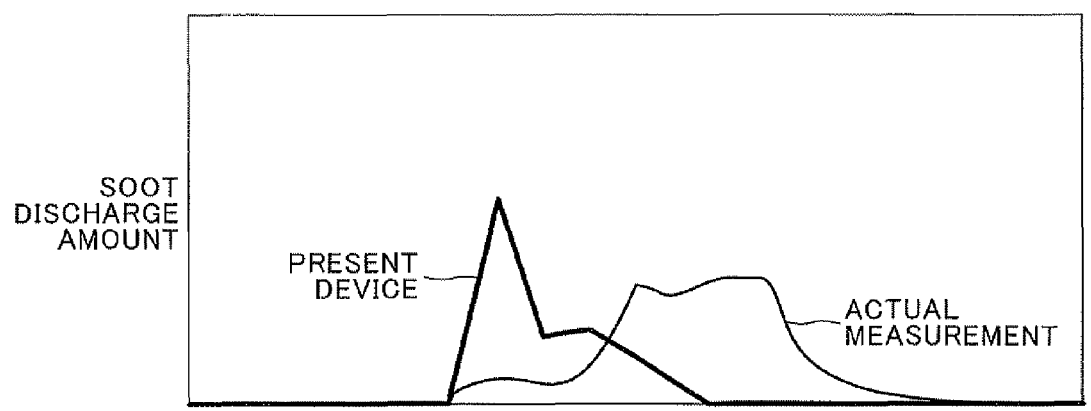

FIG. 19 shows an example (e.g., at the time of sharp acceleration) of changes in Roxc's, Roxc't, B2's/B2't, and the soot discharge amount in the case where Roxc's, Roxc't, B2's, and B2't are set as described above. As shown in FIG. 19, even when Roxc't greatly deviates from Roxc's in a transient operation state, such as at the time of sharp acceleration, by means of multiplying the steady discharge amount by "B2's/B2't," the soot discharge amount can change without greatly deviating from an actually measured value.

As described above, since the ratio B2's/B2't is taken into consideration in the oxidation correction term as shown in the above-described Eq. (10), it becomes possible to express that the combustion gas intake ratio X (=Gs/Gcyl) increases when oxygen within the cylinder tends to become insufficient transiently (for example, when the in-cylinder gas amount Gcyl is small or when the in-cylinder oxygen concentration Roxc is low), and that, when the oxygen within the cylinder tends to become insufficient transiently, the soot oxidation speed decreases, and the soot discharge amount increases.

That is, by means of using the "ratio B2's/B2't based on Roxc'" in the oxidation correction term instead of the "ratio B2s/B2t based on Roxc," there can be attained actions and effects similar to those attained through addition of the "ratio C1t/C1s based on X" as the mixing correction term in the above-described first embodiment.

<<B3s/B3t Based on Oxidation Region Representative Temperature To2>>

The oxidation region representative temperature To2 is a temperature which represents different temperatures at different locations within fuel mist; in particular, a representative temperature within the fuel mist (gas mixture) in the second half of combustion of fuel; i.e., in a state in which the fuel mist has dispersed sufficiently, the gas mixture has become uniform, and the combustion has almost ended.

The temperature within the fuel mist in the second half of combustion is considered to have a strong correlation with the above-mentioned maximum flame temperature Tmax and exhaust gas temperature Te. Therefore, in the present example, as shown in the following Eq. (15), the average between the maximum flame temperature Tmax and the exhaust gas temperature Te, or the like can be employed as the oxidation region representative temperature To2.

$$To2=(Tmax+Te) \quad (15)$$

As described above, the steady value To2$s$ of the oxidation region representative temperature To2 is obtained, through table search, from a previously created table MapTo2$s$ (NE, q), the current value (instantaneous value) of the engine speed NE, and the current value (value at this time) of the fuel injection amount q.

The transient value To2$t$ of the oxidation region representative temperature To2 can be obtained from the above-described Eq. (15). As described above, Tmax can be obtained, by use of a known method, from the intake gas temperature, the intake gas pressure, and the intake gas oxygen concentration, which can be detected by the above-described sensors; the above-described in-cylinder gas amount; etc. Also, Te can be obtained from the exhaust gas temperature sensor 77.

Figure 20:
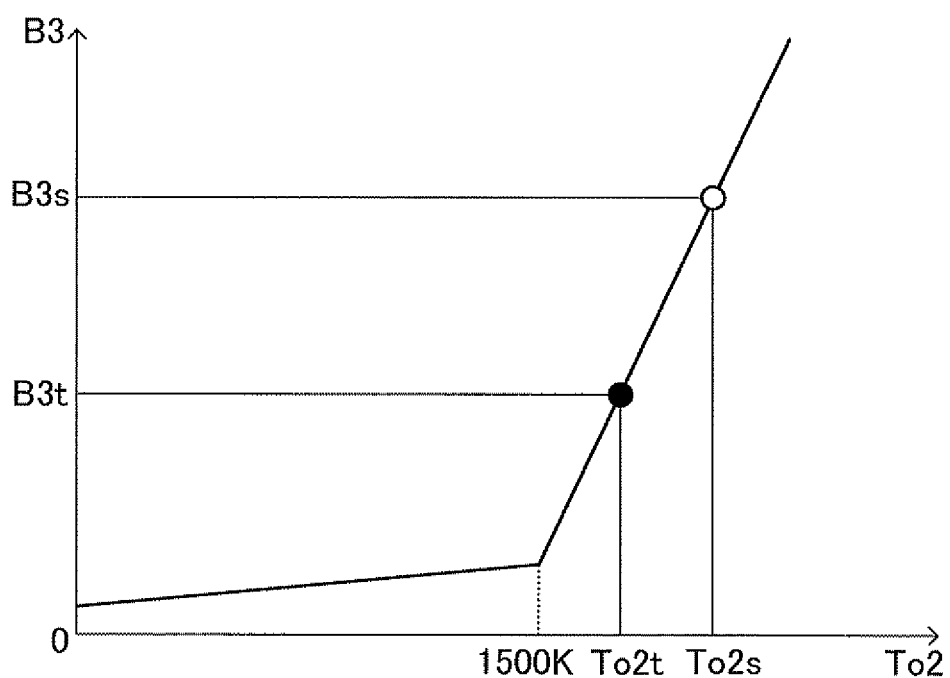
FIG. 20 is a graph showing a change in a "characteristic value B3 regarding the soot discharge amount" with oxidation region representative temperature To2.

In the present example, a characteristic equation for obtaining the "characteristic value B3 regarding the soot discharge amount" for the oxidation region representative temperature To2 is represented by the following Eq. (16), which is similar to the above-described Eq. (6). q3, q4, h3, and h4 are positive constants (q4>q3). FIG. 20 shows a change in the characteristic value B3 with To2. As shown in FIG. 20, the characteristic value B3 is very small when To2 is lower than 1500K, and substantially increases with To2 when To2 becomes equal to or higher than 1500K. The reason for employment of such a characteristic is that, even in the second half of combustion, most of soot oxidation reactions occur at temperatures equal to or higher than 1500K, and the soot oxidation reaction speed increases with temperature when the temperature is equal to or higher than 1500K.

$$B3=q3 \cdot To2+h3 \; (To2 \leq 1500K)$$

$$q4 \cdot To2-h4 \; (To2>1500K) \quad (16)$$

As shown in FIG. 20, the steady characteristic value B3$s$ is obtained from the steady value To2$s$ and Eq. (16) (that is, through substitution of To2$s$ for To2 of Eq. (16)) (see a large white circle); and the transient characteristic value B3$t$ is obtained from the transient value To2$t$ and Eq. (16) (that is, through substitution of To2$t$ for To2 of Eq. (16)) (see a large black circle).

Then, "B3$s$/B3$t$," which is the "ratio between the steady characteristic value and the transient characteristic value," is calculated (see Eq. (10)). This "B3$s$/B3$t$" represents the degree of deviation of the soot discharge amount (instantaneous value) from the steady discharge amount attributable to the "deviation of the transient value To2$t$ from the steady value To2$s$" in the transient operation state.

As described above, different temperatures at different potions within fuel mist in the second half of combustion are represented by a single temperature To2. Through this procedure, without increasing the calculation load, "B3$s$/B3$t$" can be calculated as a value which accurately represents the degree of deviation of the soot discharge amount (instantaneous value) from the steady discharge amount attributable to the "deviation of the transient value To2$t$ from the steady value To2$s$" in a transient operation state.

In addition, it is possible to express that, when the maximum flame temperature Tmax (accordingly, the oxidation region representative temperature To2) decreases as a result of a decrease in the in-cylinder oxygen concentration Roxc, the in-cylinder oxygen concentration decreases, and the degree of oxidation of soot in the second half of combustion decreases (accordingly, the soot discharge amount increases).

<<B4$s$/B4$t$ Based on In-Cylinder Oxygen Concentration Roxe>>

The in-cylinder oxygen concentration Roxe is the oxygen concentration of gas within the combustion chamber in the second half of combustion. In the second half of combustion, the oxygen concentration of gas within the combustion chamber is considered to be approximately equal to the oxygen concentration of exhaust gas. Accordingly, the in-cylinder oxygen concentration Roxe can be obtained from means for detecting or estimating the oxygen concentration of exhaust gas. The oxygen concentration of exhaust gas may be detected from an unillustrated exhaust gas oxygen concentration sensor for detecting the oxygen concentration of exhaust gas discharged from the combustion chamber, or estimated by means of subtracting, from the intake gas oxygen concentration obtained from the intake gas oxygen concentration sensor 74, a value corresponding to the amount of oxygen consumed as a result of combustion of fuel.

As described above, the steady value Roxes of the in-cylinder oxygen concentration Roxe is obtained, through table search, from a previously created table MapRoxes (NE, q), the current value (instantaneous value) of the engine speed NE, and the current value (value at this time) of the fuel injection amount q.

The transient value Roxe$t$ of the in-cylinder oxygen concentration Roxe can be obtained from the exhaust gas oxygen concentration sensor, the intake gas oxygen concentration sensor 74, or the like, as described above.

Figure 21:
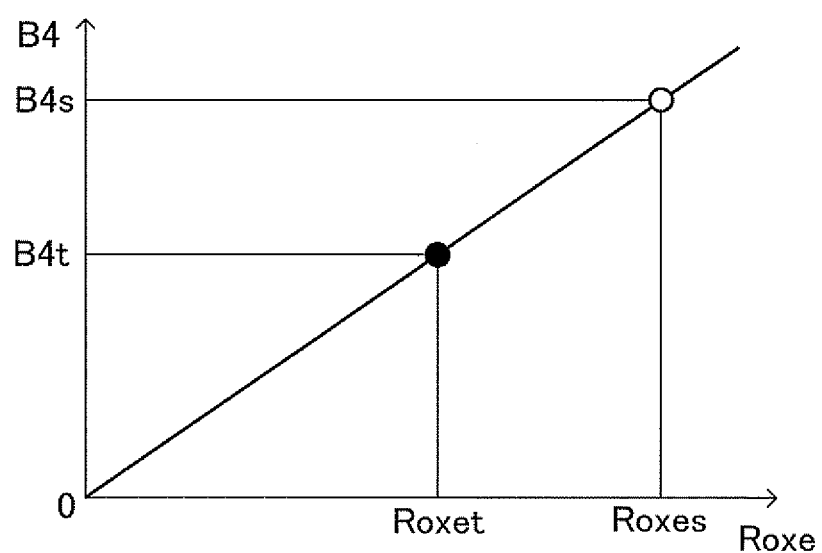
FIG. 21 is a graph showing a change in a "characteristic value B4 regarding the soot discharge amount" with in-cylinder oxygen concentration Roxe.

In the present example, a characteristic equation for obtaining the "characteristic value B4 regarding the soot discharge amount" for the in-cylinder oxygen concentration Roxe is represented by the following Eq. (17). FIG. 21 shows a change in the characteristic value B4 with Roxe. The reason for employment of Eq. (17) is that, even in the second half of the combustion, the soot oxidation speed changes in proportion to the in-cylinder oxygen concentration.

$$B4=Roxe \quad (17)$$

As shown in FIG. 21, the steady characteristic value B4$s$ is obtained from the steady value Roxes and Eq. (17) (that is, through substitution of Roxes for Roxe of Eq. (17)) (see a large white circle); and the transient characteristic value B4$t$ is obtained from the transient value Roxe$t$ and Eq. (17) (that is, through substitution of Roxe$t$ for Roxe of Eq. (17)) (see a large black circle).

Then, "B4$s$/B4$t$," which is the "ratio between the steady characteristic value and the transient characteristic value," is calculated (see Eq. (10)). This "B4$s$/B4$t$" accurately represents the degree of deviation of the soot discharge amount (instantaneous value) from the steady discharge amount attributable to the "deviation of the transient value Roxe$t$ from the steady value Roxes" in the transient operation state.

<<Weighting Coefficient α>>

The ratio between oxidation amount (degree of oxidation) of soot in the first half of combustion and that in the second half of combustion is considered to be approximately equal to the ratio between the soot oxidation speed in the first half of combustion and that in the second half of combustion. The soot oxidation speed in the first half of combustion can be represented by the characteristic value B1 regarding the above-mentioned oxidation region representative temperature To1 (see FIG. 10 and Eq. (6)), and the soot oxidation speed in the second half of combustion can be represented by the characteristic value B3 regarding the above-mentioned oxidation region representative temperature To2 (see FIG. 20 and Eq. (16)). From the above, for example, the weighting coefficient α can be expressed by the following Eq. (18) or (19) on the basis of the oxidation region representative temperature To1 or To2.

$$\alpha = \frac{B1t}{B1t + B3t} \quad (18)$$

$$\alpha = \frac{B1s}{B1s + B3s} \quad (19)$$

Notably, in general, the oxidation region representative temperature To1 in the first half of combustion is higher than 1500K, and the oxidation region representative temperature To2 in the second half of combustion is lower than 1500K. Therefore, the characteristic value B3 (B3t, B3s) becomes very small as compared with the characteristic value B1 (B1t, B1s). Accordingly, in view of the above, the weighting coefficient α may be set to 1 (constant).

Furthermore, when the in-cylinder oxygen concentration Roxc (intake gas oxygen concentration) is high, the maximum flame temperature increases, and oxidation of soot proceeds easily in both the first half of combustion and the second half of combustion. Meanwhile, when the in-cylinder oxygen concentration Roxc is low, the maximum flame temperature decrease. Therefore, in the second half of combustion, which is lower in temperature than the first half of combustion, oxidation of soot becomes relatively difficult to proceed as compared with the first half of combustion. In other words, the lower the in-cylinder oxygen concentration Roxc, the greater the ratio (=α) of the oxidation amount of soot in the first half of combustion to the total oxidation amount of soot.

In addition, when the in-cylinder pressure Pc (intake gas pressure is high, dispersion of fuel mist becomes difficult, and oxidation of soot proceeds relatively easily in the first half of combustion. Meanwhile, when the in-cylinder pressure Pc is low, fuel mist disperses easily, oxidation of soot proceeds relatively easily in the second half of combustion. In other words, the higher the in-cylinder pressure Pc, the greater the ratio (=α) of the oxidation amount of soot in the first half of combustion to the total oxidation amount of soot.

Figure 22:
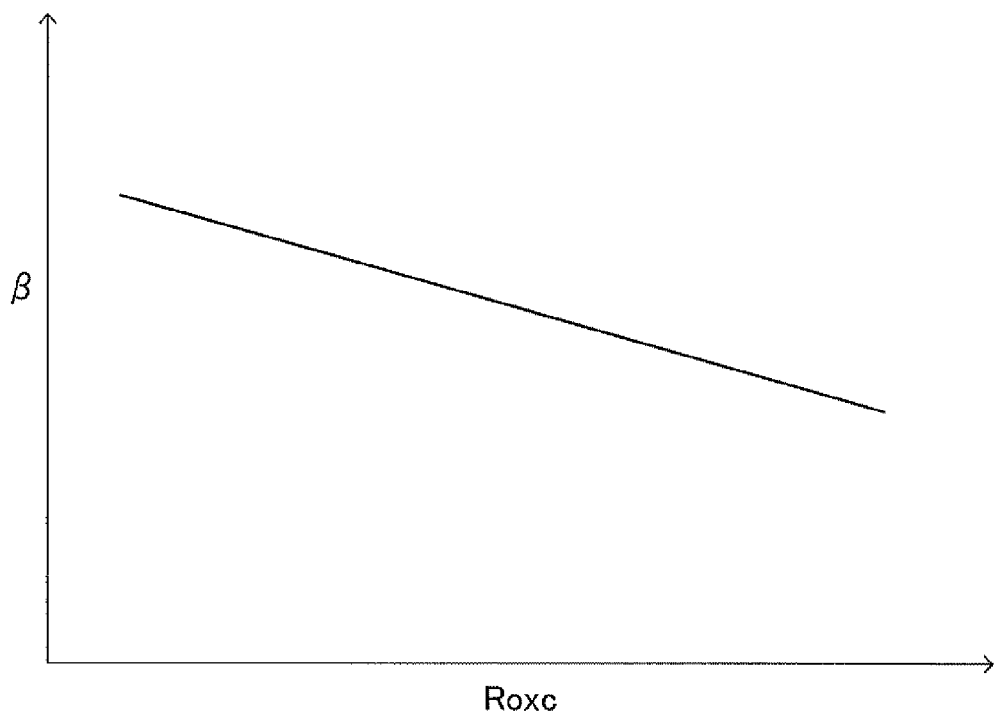
FIG. 22 is a graph showing a table used for determination of a coefficient $\beta$ used for calculation of a weighting coefficient $\alpha$.
Figure 23:
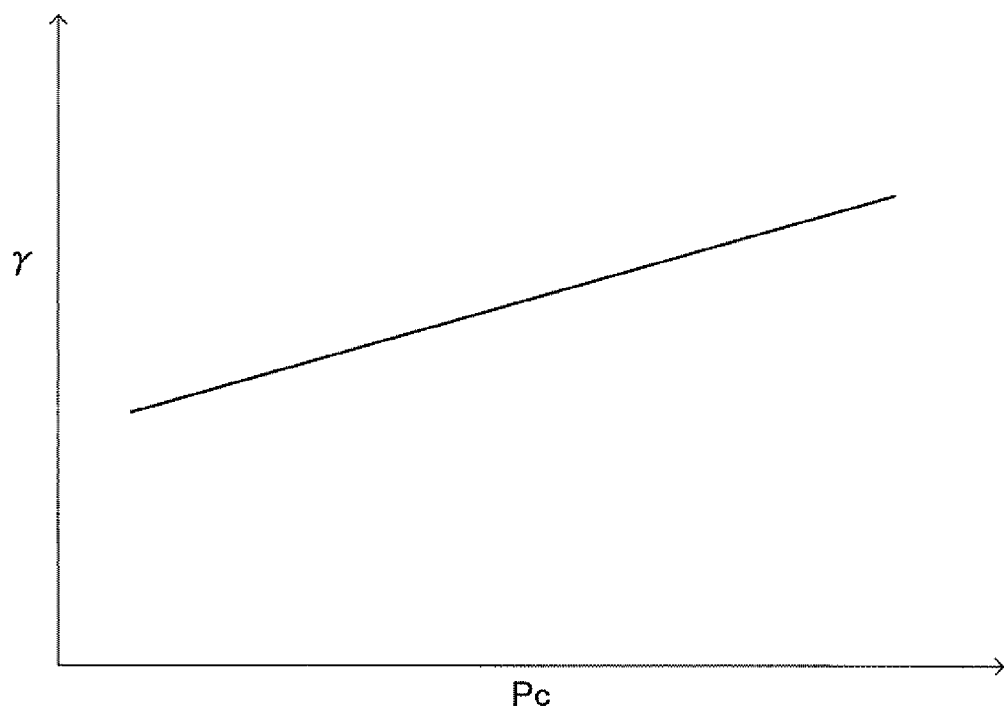
FIG. 23 is a graph showing a table used for determination of a coefficient $\gamma$ used for calculation of the weighting coefficient $\alpha$.

From the above, the weighting coefficient α can be represented, for example, by the following Eq. (20) on the basis of the in-cylinder oxygen concentration Roxc and the in-cylinder pressure Pc. In Eq. (20), β is a coefficient determined on the basis of a table shown in FIG. 22 such that the lower the in-cylinder oxygen concentration Roxc, the greater the coefficient β. γ is a coefficient determined on the basis of a table shown in FIG. 23 such that the higher the in-cylinder pressure Pc, the greater the coefficient γ. Notably, the weighting coefficient α may be determined on the basis of only one of the in-cylinder oxygen concentration Roxc and the in-cylinder pressure Pc; i.e., the weighting coefficient α may be determined such that α=β, or α=γ.

$$\alpha = \beta \cdot \gamma \quad (20)$$

As described above, in the oxidation correction term, the "ratio B1s/B1t based on the oxidation region representative temperature To1" and the "ratio B2′s/B2′t based on the net in-cylinder oxygen concentration Roxc′" are used for the first half of combustion, and the "ratio B3s/B3t based on the oxidation region representative temperature To2" and the "ratio B4s/B4t based on the in-cylinder oxygen concentration Roxe" are used for the second half of combustion. However, the present embodiment may be modified to use only one of the "ratio B1s/B1t based on the oxidation region representative temperature To1" and the "ratio B2′s/B2′t based on the net in-cylinder oxygen concentration Roxc′" for the first half of combustion, and use only one of the "ratio B3s/B3t based on the oxidation region representative temperature To2" and the "ratio B4s/B4t based on the in-cylinder oxygen concentration Roxe" for the second half of combustion.

Soot Discharge Amount Estimation Method According to a Third Embodiment

Next, a soot discharge amount estimation method according to a third embodiment of the soot discharge estimating device of the present invention will be described. This third embodiment differs from the second embodiment only in the point that the transient correction value is calculated from the following Eq. (21), in contrast to the second embodiment in which the transient correction value is calculated from the above-described Eq. (10). In the following, only the difference will be described.

$$\text{Transient correction value} = \underbrace{\frac{A1t}{A1s} \cdot \frac{A2t}{A2s} \cdot \frac{A3t}{A3s}}_{\text{Generation correction}} \cdot \underbrace{\frac{B1s}{B1t} \cdot \frac{B5t}{B5s}}_{\text{Oxidation correction}} \quad (21)$$

As can be understood from Eq. (21), as in the second embodiment, the third embodiment is configured such that the transient correction value is calculated from the generation correction term and the oxidation correction term only. Furthermore, the generation correction term is identical with that used in the second embodiment. Meanwhile, in the oxidation correction term, a "ratio B5t/B5s based on mist overlapping degree L," which is peculiar to the third embodiment, is used in addition to the "ratio B1s/B1t based on the oxidation region representative temperature to1," which is used in the first and second embodiments.

<<B5t/B5s Based on Mist Overlapping Degree L>>

In actuality, due to the shape of the combustion chamber (shape of the cavity), etc., the in-cylinder gas has a portion to which fuel mist does not reach (which does not mix with fuel mist) (a portion that does not contribute to combustion of fuel). Here, a ratio of a portion of the in-cylinder gas which can mix with fuel mist (contributes combustion of fuel) to the entire in-cylinder gas will be referred to as an "air utilization factor," and the "amount of gas within the combustion chamber, excluding a portion of the gas that does not contribute to combustion of fuel," is referred to as Gcyl′. The Gcyl′ can be represented by the following Eq. (22).

$$Gcyl' = Gcyl \cdot (\text{air utilization factor}) \quad (22)$$

Figure 24:
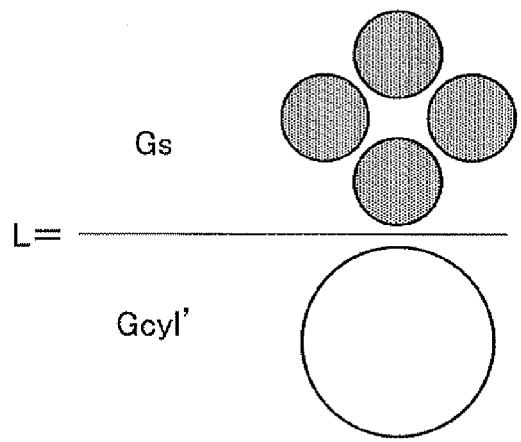
FIG. 24 is a diagram showing an equation which defines a mist overlapping degree L.

Through use of this Gcyl′ and the above-mentioned "in-cylinder gas amount Gs" required for complete combustion of all fuel of the fuel injection amount q, "a mist overlapping degree L=Gs/Gcyl′ is defined as shown in FIG. 24.

Figure 25:
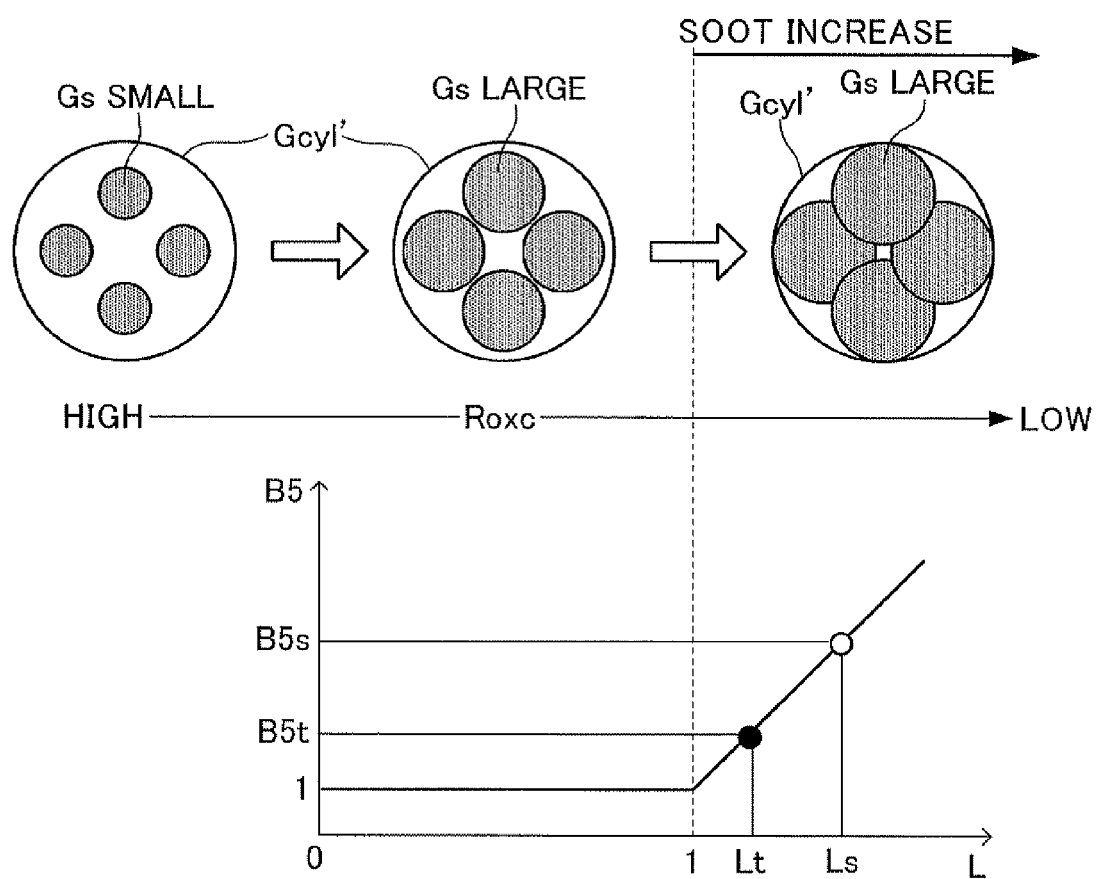
FIG. 25 is a diagram used for explaining the relation among the in-cylinder gas amount Gs required for complete combustion of all fuel, the in-cylinder oxygen concentration Roxc, and the mist overlapping degree L.

As shown in FIG. 25, like the above-mentioned "combustion gas intake ratio X," the mist overlapping degree L increases as the in-cylinder oxygen concentration Roxc decreases. Since a "portion of the in-cylinder gas that does not contribute to combustion of fuel" is taken into consideration, the value of L may exceed "1" in some cases.

As shown in FIG. 25, the greater the mist overlapping degree L (especially, when L>1), the higher the probability of overlapping of fuel mists injected from a plurality of injection holes (four injection holes in FIG. 25). In regions where the fuel mists overlap with one another, it becomes difficult for oxygen to be taken in the fuel mists, whereby the soot oxidation speed decreases in these regions. As can be understood from the above, the mist overlapping degree L can serve as a factor that strongly affects the soot oxidation speed.

As described above, the steady value Ls of the mist overlapping degree L is obtained, through table search, from a previously created table MapLs (NE, q), the current value (instantaneous value) of the engine speed NE, and the current value (value at this time) of the fuel injection amount q. The transient value Lt of the mist overlapping degree L is obtained in accordance with the equation shown in FIG. 24.

In the present example, a characteristic equation for obtaining the "characteristic value B5 regarding the soot discharge amount" for the mist overlapping degree L is represented by the following Eq. (23). q5 and h5 are positive constants. FIG. 25 shows a change in the characteristic value B5 with L. The reason for employment of Eq. (23) is that, as described above, when L>1, the probability of mutual overlapping of fuel mists increases, and the soot oxidation speed decreases.

$$B5 = 1 (L \leq 1)$$
$$= q5 \cdot L - h5 (L > 1) \quad (23)$$

As shown in FIG. 25, the steady characteristic value B5s is obtained from the steady value Ls and Eq. (23) (that is, through substitution of Ls for L of Eq. (23)) (see a large white circle); and the transient characteristic value B5t is obtained from the transient value Lt and Eq. (23) (that is, through substitution of Lt for L of Eq. (23)) (see a large black circle).

Then, "B5t/B5s," which is the "ratio between the steady characteristic value and the transient characteristic value," is calculated (see Eq. (21)). This "B5t/B5s" represents the degree of deviation of the soot discharge amount (instantaneous value) from the steady discharge amount attributable to the "deviation of the transient value Lt from the steady value Ls" in the transient operation state.

As described above, through addition of "B5t/B5s" to the oxidation correction term of the above-described Eq. (21), it becomes possible to express that the mist overlapping degree L (=Gs/Gcyl') increases when the probability of mutual overlapping of fuel mists is transiently high (for example, when the in-cylinder gas amount Gcyl is small or when the in-cylinder oxygen concentration Roxc is low), and that, when the probability of mutual overlapping of fuel mists is transiently high, the soot discharge amount increases.

Soot Discharge Amount Estimation Method According to a Fourth Embodiment

Next, a soot discharge amount estimation method according to a fourth embodiment of the soot discharge estimating device of the present invention will be described. This fourth embodiment differs from the first embodiment only in the point that the transient correction value is calculated from the following Eq. (24), in contrast to the first embodiment in which the transient correction value is calculated from the above-described Eq. (2). In the following, only the difference will be described.

$$\text{Transient correction value} = \frac{A1t}{A1s} \cdot \frac{A2t}{A2s} \cdot \frac{A4t}{A4s} \cdot \frac{B1s}{B1t} \cdot \frac{B2t}{B2s} \quad (24)$$

As can be understood from Eq. (24), in the fourth embodiment, the transient correction value is calculated from the generation correction term and the oxidation correction term only. The present embodiment is identical with the first embodiment in that the "ratio A1t/A1s based on the fuel mist representative temperature Tf" and the "ratio A2t/A2s based on the in-cylinder pressure Pc" are used in the generation correction term, but differs from the first embodiment in that, in placed of the "ratio A3t/A3s based on the in-cylinder oxygen concentration Roxc," a "ratio A4t/A4s based on an ignition delay period ID" is introduced. The ignition delay period ID refers to a period (crank angle or time) between a point in time when fuel injection starts (in the case where pilot injection is performed prior to main injection, a point in time when the main injection starts) and a point in time when ignition starts.

<<A4t/A4s Based on Ignition Delay Period ID>>

Figure 26:
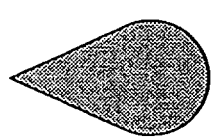
FIG. 26 is an illustration used for explaining the relation among the ignition delay period, the average equivalence ratio of mist, and the soot discharge amount.
Figure 26:
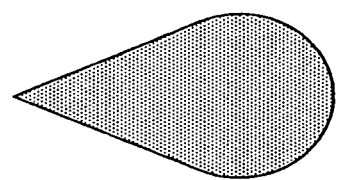

As shown in FIG. 26, when the ignition delay period ID is short, the size of fuel mist at the ignition start time deceases, and the (average) equivalence ratio of fuel mist at the ignition start time increases. As a result, the generation of soot occurs more easily. As can be understood from the above, the ignition delay period ID serves as a "factor that affects the soot generation speed." The ignition delay period ID can be calculated, for example, by use of an ignition start time determined on the basis of changes in the in-cylinder pressure detected from the in-cylinder pressure sensor 75. Alternatively, the ignition delay period ID can be estimated by use of one of known estimation methods.

Figure 27:
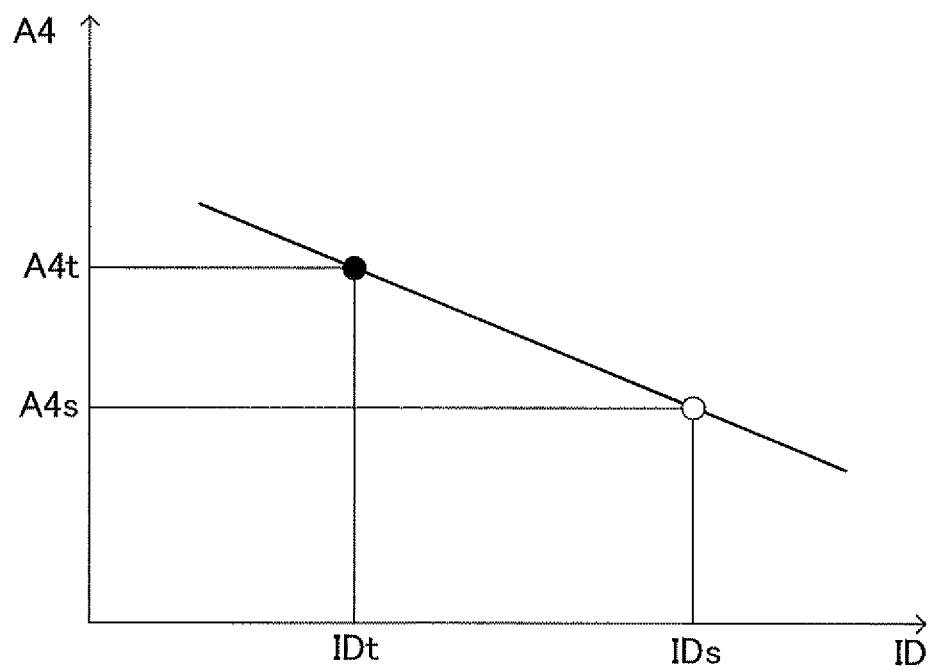
FIG. 27 is a graph showing a change in a "characteristic value A4 regarding the soot discharge amount" with ignition delay period ID.

In the present example, a characteristic equation for obtaining the "characteristic value A4 regarding the soot discharge amount" for the ignition delay period ID is represented by the following Eq. (25). q6 is a negative constant, and h6 is a positive constant. FIG. 27 shows a change in the characteristic value A4 with ID. The reason for employment of Eq. (25) is that, as described above, the shorter the ignition delay period ID, the more readily soot is produced. Notably, a characteristic equation (representing a downwardly convexed curve or an upwardly convexed curve) different from Eq. (25) may be employed, so long as the employed characteristic equation is such that the shorter the ignition delay period ID, the greater the characteristic value.

$$A4 = q6 \cdot ID + h6 \quad (25)$$

As shown in FIG. 27, the steady characteristic value A4s is obtained from the steady value IDs and Eq. (25) (that is, through substitution of IDs for ID of Eq. (25)) (see a large white circle); and the transient characteristic value A4t is obtained from the transient value IDt and Eq. (25) (that is, through substitution of IDt for ID of Eq. (25)) (see a large black circle).

Then, "A4t/A4s," which is the "ratio between the steady characteristic value and the transient characteristic value," is calculated (see Eq. (24)). This "A4t/A4s" represents the degree of deviation of the soot discharge amount (instantaneous value) from the steady discharge amount attributable to the "deviation of the transient value IDt from the steady value IDs" in the transient operation state.

Through addition of "A4t/A4s" to the generation correction term as shown in the above-described Eq. (24), it becomes possible to express that, when the ignition delay period ID becomes short because of a certain cause (accordingly, the size of fuel mist at the ignition start time decreases), soot is produced more easily, and the soot discharge amount increases.

Various cases where, instead of the ignition delay period ID itself, a "value correlated with the ignition delay period ID" is used so as to calculate the transient correction value will now be described on a case-by-case basis.

<<A5t/A5s Based on Compression End Temperature Tcomp>>

In general, when the compression end temperature Tcomp is high, the ignition start time becomes earlier, whereby the ignition delay period ID becomes shorter. That is, the compression end temperature Tcomp is a "value correlated with the ignition delay period ID," and the higher the compression end temperature Tcomp, the more readily shoot is produced. As described above, the compression end temperature Tcomp can be obtained, by use of a known method, from the intake gas temperature, the intake gas pressure, and the intake gas oxygen concentration, which can be detected by the above-described sensors; the entire amount of gas taken in the combustion chamber (in-cylinder gas amount); etc.

In the case where the transient correction value is calculated through use of the compression end temperature Tcomp rather than the ignition delay period ID itself, the transient correction value is calculated from the following Eq. (26) rather than the above-described Eq. (24). Eq. (26) differs from the above-described Eq. (24) only in the point that, in place of the "ratio A4t/A4s based on the ignition delay period ID," a "ratio A5t/A5s based on the compression end temperature Tcomp" is introduced. In the following, only this difference will be described.

$$\text{Transient correction value} = \frac{A1t}{A1s} \cdot \frac{A2t}{A2s} \cdot \frac{A5t}{A5s} \cdot \frac{B1s}{B1t} \cdot \frac{B2t}{B2s} \quad (26)$$

Figure 28:
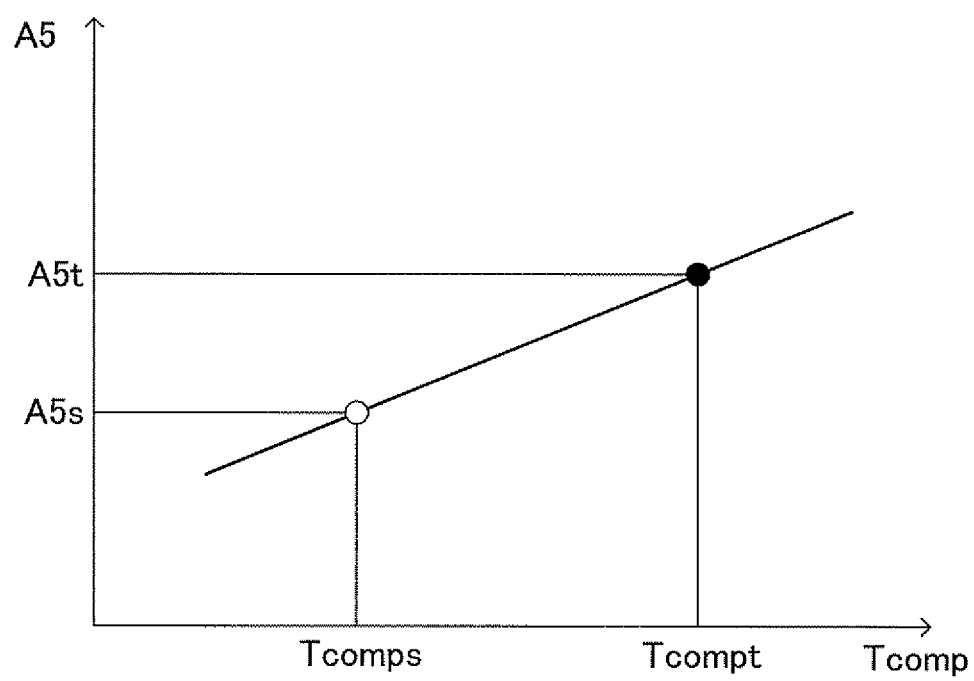
FIG. 28 is a graph showing a change in a "characteristic value A5 regarding the soot discharge amount" with compression end temperature Tcomp.

In the present example, a characteristic equation for obtaining the "characteristic value A5 regarding the soot discharge amount" for the compression end temperature Tcomp is represented by the following Eq. (27). q7 and h7 are positive constants. FIG. 28 shows a change in the characteristic value A5 with Tcomp. The reason for employment of Eq. (27) is that, as described above, the higher the compression end temperature Tcomp, the more readily soot is produced. Notably, a characteristic equation (representing a downwardly convexed curve or an upwardly convexed curve) different from Eq. (27) may be employed, so long as the employed characteristic equation is such that the higher the compression end temperature Tcomp, the greater the characteristic value.

$$A5 = q7 \cdot Tcomp + h7 \quad (27)$$

As shown in FIG. 28, the steady characteristic value A5s is obtained from the steady value Tcomps and Eq. (27) (that is, through substitution of Tcomps for Tcomp of Eq. (27)) (see a large white circle); and the transient characteristic value A5t is obtained from the transient value Tcompt and Eq. (27) (that is, through substitution of Tcompt for Tcomp of Eq. (27)) (see a large black circle).

Then, "A5t/A5s," which is the "ratio between the steady characteristic value and the transient characteristic value," is calculated (see Eq. (26)). This "A5t/A5s" represents the degree of deviation of the soot discharge amount (instantaneous value) from the steady discharge amount attributable to the "deviation of the transient value Tcompt from the steady value Tcomps" in the transient operation state. Thus, it becomes possible to calculate the transient correction value as a value determined in consideration of the influence of the length of the ignition delay period ID on the soot discharge amount, without obtaining the ignition delay period ID itself.

Through addition of "A5t/A5s" to the generation correction term as shown in the above-described Eq. (26), it becomes possible to express that, when the compression end temperature increases because of a certain cause (accordingly, the ignition delay period becomes shorter), soot is produced more easily, and the soot discharge amount increases.

<<A6t/A6s Based on Exhaust Gas Pressure Pe>>

In general, when the exhaust gas pressure Pe is high, the amount of internal EGR gas (exhaust gas circulated from the exhaust passage to the combustion chamber via the exhaust valve) increases, whereby the compression end temperature Tcomp becomes higher. As a result, the ignition delay period ID becomes shorter. That is, the exhaust gas pressure Pe serves as a "value correlated with the ignition delay period ID," and the higher the exhaust gas pressure Pe, the more readily shoot is produced. For example, the exhaust gas pressure Pe can be detected from the exhaust gas pressure sensor 81. Alternatively, the exhaust gas pressure Pe can be obtained by use of one of known estimation methods.

In the case where the transient correction value is calculated through use of the exhaust gas pressure Pe rather than the ignition delay period ID itself, the transient correction value is calculated from the following Eq. (28) rather than the above-described Eq. (24). Eq. (28) differs from the above-described Eq. (24) only in the point that, in place of the "ratio A4t/A4s based on the ignition delay period ID," a "ratio A6t/A6s based on the exhaust gas pressure Pe" is introduced. In the following, only this difference will be described.

$$\text{Transient correction value} = \frac{A1t}{A1s} \cdot \frac{A2t}{A2s} \cdot \frac{A6t}{A6s} \cdot \frac{B1s}{B1t} \cdot \frac{B2t}{B2s} \quad (28)$$

Figure 29:
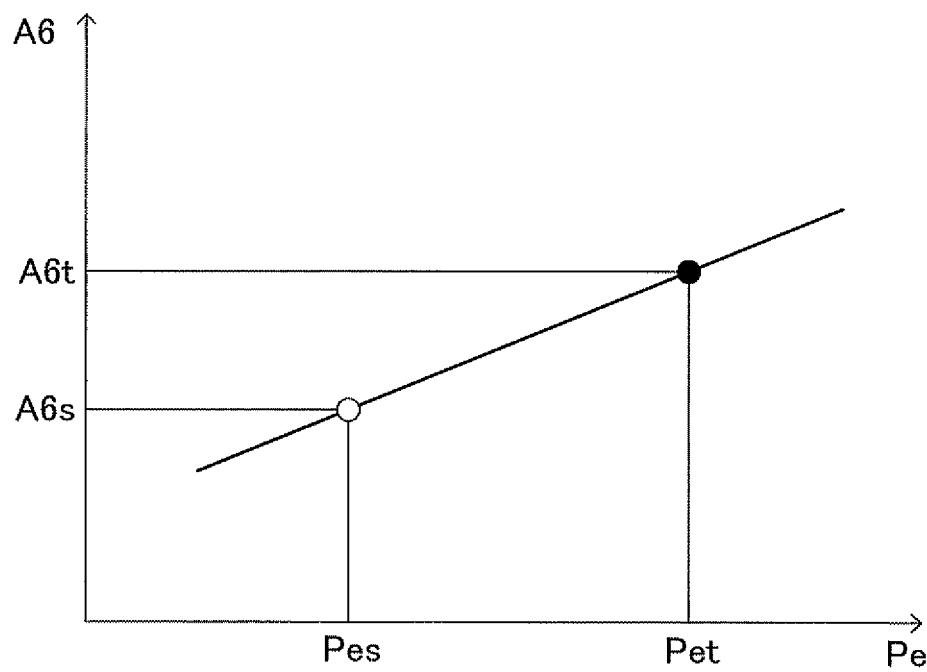
FIG. 29 is a graph showing a change in a "characteristic value A6 regarding the soot discharge amount" with exhaust gas pressure Pe.

In the present example, a characteristic equation for obtaining the "characteristic value A6 regarding the soot discharge amount" for the exhaust gas pressure Pe is represented by the following Eq. (29). q8 and h8 are positive constants. FIG. 29 shows a change in the characteristic value A6 with Pe. The reason for employment of Eq. (29) is that, as described above, the higher the exhaust gas pressure Pe, the more readily soot is produced. Notably, a characteristic equation (representing a downwardly convexed curve or an upwardly convexed curve) different from Eq. (29) may be employed, so long as the employed characteristic equation is such that the higher the exhaust gas pressure Pe, the greater the characteristic value.

$$A6 = q8 \cdot Pe + h8 \quad (29)$$

As shown in FIG. 29, the steady characteristic value A6s is obtained from the steady value Pes and Eq. (29) (that is, through substitution of Pes for Pe of Eq. (29)) (see a large white circle); and the transient characteristic value A6t is obtained from the transient value Pet and Eq. (29) (that is, through substitution of Pet for Pe of Eq. (29)) (see a large black circle).

Then, "A6t/A6s," which is the "ratio between the steady characteristic value and the transient characteristic value," is calculated (see Eq. (28)). This "A6t/A6s" represents the degree of deviation of the soot discharge amount (instantaneous value) from the steady discharge amount attributable to the "deviation of the transient value Pet from the steady value Pes" in the transient operation state. Thus, it becomes possible to calculate the transient correction value as a value determined in consideration of the influence of the length of the ignition delay period ID on the soot discharge amount, without obtaining the ignition delay period ID itself.

Through addition of "A6t/A6s" to the generation correction term as shown in the above-described Eq. (28), it becomes possible to express that, when the exhaust gas pressure increases because of a certain cause (accordingly, the ignition delay period becomes shorter), soot is produced more easily, and the soot discharge amount increases.

<<A7t/A7s Based on Exhaust Gas Temperature Te>>

In general, when the exhaust gas temperature Te is high, the temperature of the internal EGR gas becomes higher, whereby the compression end temperature Tcomp becomes higher. As a result, the ignition delay period ID becomes shorter. That is, the exhaust gas temperature Te serves as a "value correlated with the ignition delay period ID," and the higher the exhaust gas temperature Te, the more readily shoot is produced. For example, the exhaust gas temperature Te can be detected from the exhaust gas temperature sensor 77. Alternatively, the exhaust gas temperature Te can be obtained by use of one of known estimation methods.

In the case where the transient correction value is calculated through use of the exhaust gas temperature Te rather than the ignition delay period ID itself, the transient correction value is calculated from the following Eq. (30) rather than the above-described Eq. (24). Eq. (30) differs from the above-described Eq. (24) only in the point that, in place of the "ratio A4t/A4s based on the ignition delay period ID," a "ratio A7t/A7s based on the exhaust gas temperature Te" is introduced. In the following, only this difference will be described.

$$\text{Transient correction value} = \frac{A1t}{A1s} \cdot \frac{A2t}{A2s} \cdot \frac{A7t}{A7s} \cdot \frac{B1s}{B1t} \cdot \frac{B2t}{B2s} \quad (30)$$

Figure 30:
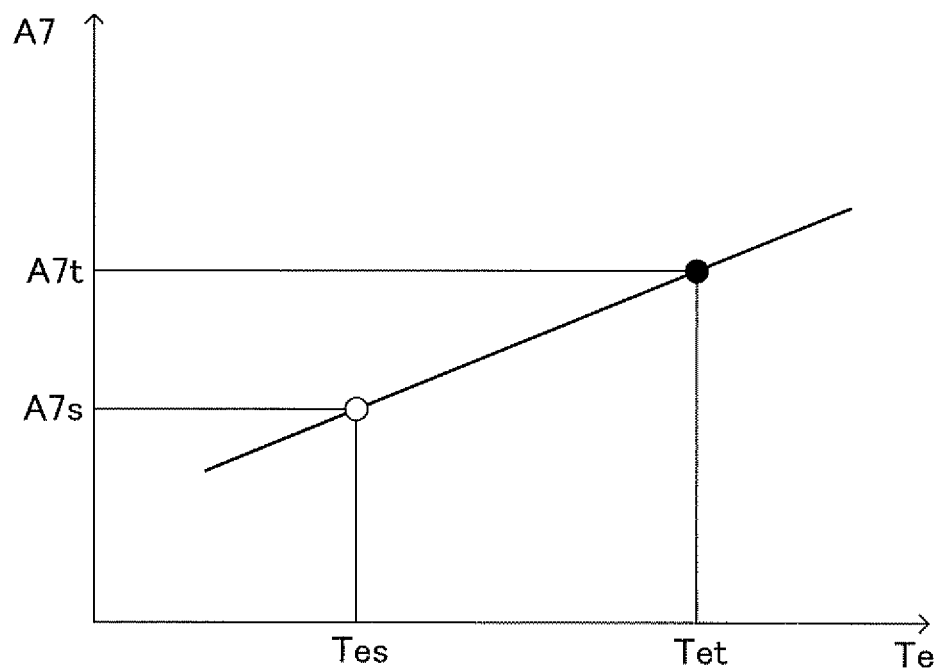
FIG. 30 is a graph showing a change in a "characteristic value A7 regarding the soot discharge amount" with exhaust gas temperature Te.

In the present example, a characteristic equation for obtaining the "characteristic value A7 regarding the soot discharge amount" for the exhaust gas temperature Te is represented by the following Eq. (31), q9 and h9 are positive constants. FIG. 30 shows a change in the characteristic value A7 with Te. The reason for employment of Eq. (31) is that, as described above, the higher the exhaust gas temperature Te, the more readily soot is produced. Notably, a characteristic equation (representing a downwardly convexed curve or an upwardly convexed curve) different from Eq. (31) may be employed, so long as the employed characteristic equation is such that the higher the exhaust gas temperature Te, the greater the characteristic value.

$$A7 = q9 \cdot Te + h9 \quad (31)$$

As shown in FIG. 30, the steady characteristic value A7s is obtained from the steady value Tes and Eq. (31) (that is, through substitution of Tes for Te of Eq. (31)) (see a large white circle); and the transient characteristic value A7t is obtained from the transient value Tet and Eq. (31) (that is, through substitution of Tet for Te of Eq. (31)) (see a large black circle).

Then, "A7t/A7s," which is the "ratio between the steady characteristic value and the transient characteristic value," is calculated (see Eq. (30)). This "A7t/A7s" represents the degree of deviation of the soot discharge amount (instantaneous value) from the steady discharge amount attributable to the "deviation of the transient value Tet from the steady value Tes" in the transient operation state. Thus, it becomes possible to calculate the transient correction value as a value determined in consideration of the influence of the length of the ignition delay period ID on the soot discharge amount, without obtaining the ignition delay period ID itself.

Through addition of "A7t/A7s" to the generation correction term as shown in the above-described Eq. (30), it becomes possible to express that, when the exhaust gas temperature increases because of a certain cause (accordingly, the ignition delay period becomes shorter), soot is produced more easily, and the soot discharge amount increases.

<<A8t/A8s Based on Intake Gas Temperature Ti>>

In general, when the intake gas temperature Ti is high, the compression end temperature Tcomp becomes higher. As a result, the ignition delay period ID becomes shorter. That is, the intake gas temperature Ti serves as a "value correlated with the ignition delay period ID," and the higher the intake gas temperature Ti, the more readily shoot is produced. For example, the intake gas temperature Ti can be detected from the intake gas temperature sensor 72. Alternatively, the intake gas temperature Ti can be obtained by use of one of known estimation methods.

In the case where the transient correction value is calculated through use of the intake gas temperature Ti rather than the ignition delay period ID itself, the transient correction value is calculated from the following Eq. (32) rather than the above-described Eq. (24). Eq. (32) differs from the above-described Eq. (24) only in the point that, in place of the "ratio A4t/A4s based on the ignition delay period ID," a "ratio A8t/A8s based on the intake gas temperature Ti" is introduced. In the following, only this difference will be described.

$$\text{Transient correction value} = \frac{A1t}{A1s} \cdot \frac{A2t}{A2s} \cdot \frac{A8t}{A8s} \cdot \frac{B1s}{B1t} \cdot \frac{B2t}{B2s} \quad (32)$$

Figure 31:
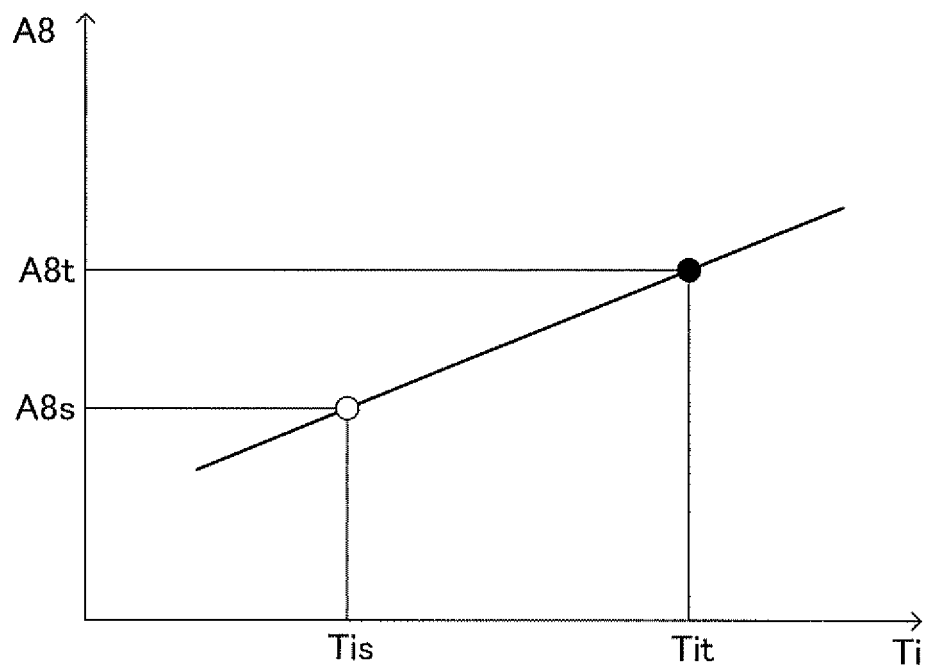
FIG. 31 is a graph showing a change in a "characteristic value A8 regarding the soot discharge amount" with intake gas temperature Ti.

In the present example, a characteristic equation for obtaining the "characteristic value A8 regarding the soot discharge amount" for the intake gas temperature Ti is represented by the following Eq. (33). q10 and h10 are positive constants. FIG. 31 shows a change in the characteristic value A8 with Ti. The reason for employment of Eq. (33) is that, as described above, the higher the intake gas temperature Ti, the more readily soot is produced. Notably, a characteristic equation (representing a downwardly convexed curve or an upwardly convexed curve) different from Eq. (33) may be employed, so long as the employed characteristic equation is such that the higher the intake gas temperature Ti, the greater the characteristic value.

$$A8 = q10 \cdot Ti + h10 \quad (33)$$

As shown in FIG. 31, the steady characteristic value A8s is obtained from the steady value Tis and Eq. (33) (that is, through substitution of Tis for Ti of Eq. (33)) (see a large white circle); and the transient characteristic value A8t is obtained from the transient value Tit and Eq. (33) (that is, through substitution of Tit for Ti of Eq. (33)) (see a large black circle).

Then, "A8t/A8s," which is the "ratio between the steady characteristic value and the transient characteristic value," is calculated (see Eq. (32)). This "A8t/A8" represents the degree of deviation of the soot discharge amount (instantaneous value) from the steady discharge amount attributable to the "deviation of the transient value Tit from the steady value Tis" in the transient operation state. Thus, it becomes possible to calculate the transient correction value as a value determined in consideration of the influence of the length of the ignition delay period ID on the soot discharge amount, without obtaining the ignition delay period ID itself.

Through addition of "A8t/A8" to the generation correction term as shown in the above-described Eq. (32), it becomes possible to express that, when the intake gas temperature increases because of a certain cause (accordingly, the ignition delay period becomes shorter), soot is produced more easily, and the soot discharge amount increases.

<<A9t/A9s based on Temperature Tz>>

As described above, both the exhaust gas temperature Te and the intake gas temperature Ti can serve as a "value correlated with the ignition delay period ID." Here, the ratio of the amount of the internal EGR gas to the sum of the amount of the internal EGR gas and the amount of external EGR gas (exhaust gas circulated from the exhaust passage to the combustion chamber via an exhaust gas circulation passage connecting the exhaust passage and the intake passage together) will be referred to as "an internal EGR ratio r."

The degree of influence of the exhaust gas temperature Te on the compression end temperature Tcomp (accordingly, the ignition delay period ID) greatly depends on the internal EGR ratio r, and the greater the internal EGR ratio r, the greater the degree of the influence. Meanwhile, the degree of influence of the intake gas temperature Ti on the compression end temperature Tcomp (accordingly, the ignition delay period ID) greatly depends on the value of (1−r), and the greater the value of (1−r), the greater the degree of the influence. In view of the above, a temperature Tz is defined as shown in the following Eq. (34).

$$Tz = r \cdot Te + (1-r) \cdot Ti \tag{34}$$

As can be understood from Eq. (34), the temperature Tz is a value which is obtained in consideration of the exhaust gas temperature Te, the intake gas temperature Ti, and the internal EGR ratio r. Therefore, the temperature Tz can be said to be a temperature determined in consideration of the degrees of influence of the exhaust gas temperature Te and the intake gas temperature Ti on the compression end temperature Tcomp (accordingly, the degrees of influence on the ignition delay period ID). Notably, the internal EGR ratio r can be obtained by use of one of known estimation methods.

When the temperature Tz is high, the compression end temperature Tcomp becomes higher. As a result, the ignition delay period ID becomes shorter. That is, the temperature Tz serves as a "value correlated with the ignition delay period ID," and the higher the temperature Tz, the more readily shoot is produced.

In the case where the transient correction value is calculated through use of the temperature Tz rather than the ignition delay period ID itself, the transient correction value is calculated from the following Eq. (35) rather than the above-described Eq. (24). Eq. (35) differs from the above-described Eq. (24) only in the point that, in place of the "ratio A4t/A4s based on the ignition delay period ID," a "ratio A9t/A9s based on the temperature Tz" is introduced. In the following, only this difference will be described.

$$\text{Transient correction value} = \frac{A1t}{A1s} \cdot \frac{A2t}{A2s} \cdot \frac{A9t}{A9s} \cdot \frac{B1s}{B1t} \cdot \frac{B2t}{B2s} \tag{35}$$

Figure 32:
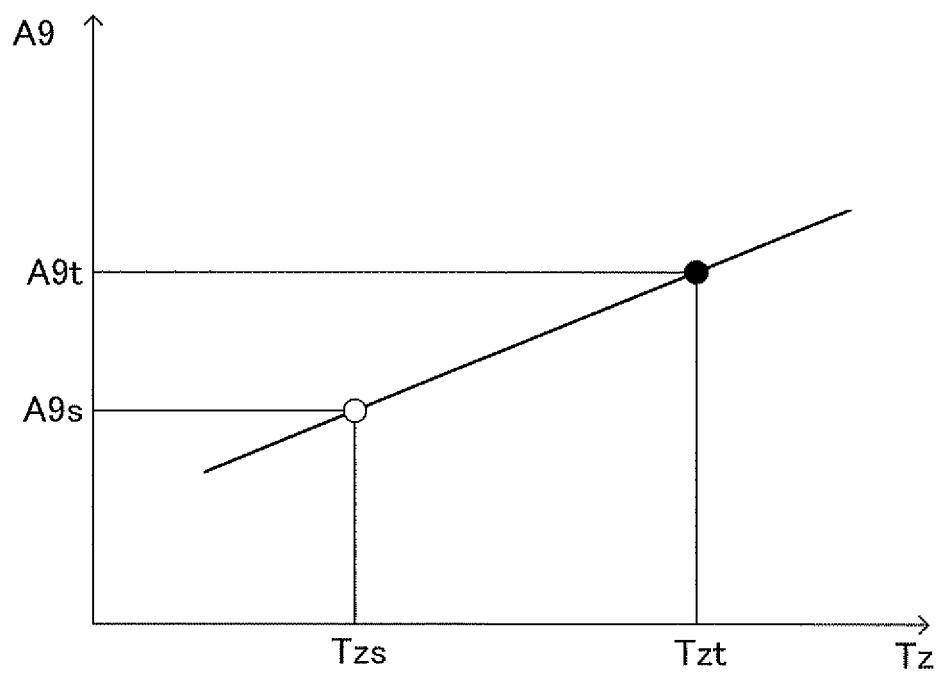
FIG. 32 is a graph showing a change in a "characteristic value A9 regarding the soot discharge amount" with temperature Tz determined in consideration of the exhaust gas temperature Te, the intake gas temperature Ti, and an internal EGR ratio r.

In the present example, a characteristic equation for obtaining the "characteristic value A9 regarding the soot discharge amount" for the temperature Tz is represented by the following Eq. (36). q11 and h11 are positive constants. FIG. 32 shows a change in the characteristic value A9 with Tz. The reason for employment of Eq. (36) is that, as described above, the higher the temperature Tz, the more readily soot is produced. Notably, a characteristic equation (representing a downwardly convexed curve or an upwardly convexed curve) different from Eq. (36) may be employed, so long as the employed characteristic equation is such that the higher the temperature Tz, the greater the characteristic value.

$$A9 = q11 \cdot Tz + h11 \tag{36}$$

As shown in FIG. 32, the steady characteristic value A9s is obtained from the steady value Tzs and Eq. (36) (that is, through substitution of Tzs for Tz of Eq. (36)) (see a large white circle); and the transient characteristic value A9t is obtained from the transient value Tzt and Eq. (36) (that is, through substitution of Tzt for Tz of Eq. (36)) (see a large black circle).

Then, "A9t/A9s," which is the "ratio between the steady characteristic value and the transient characteristic value," is calculated (see Eq. (35)). This "A9t/A9s" represents the degree of deviation of the soot discharge amount (instantaneous value) from the steady discharge amount attributable to the "deviation of the transient value Tzt from the steady value Tzs" in the transient operation state. Thus, it becomes possible to calculate, without obtaining the ignition delay period ID itself, the transient correction value as a value determined in consideration of the influence of the length of the ignition delay period ID on the soot discharge amount, and in consideration of the degrees of influence of the exhaust gas temperature Te and the intake gas temperature Ti on the compression end temperature Tcomp (accordingly, on the ignition delay period ID).

Through addition of "A9t/A9s" to the generation correction term as shown in the above-described Eq. (35), it becomes possible to express that, when the temperature Tz increases because of a certain cause (accordingly, the ignition delay period becomes shorter), soot is produced more easily, and the soot discharge amount increases. Notably, in the above-described Eq. (35), the "ratio A9t/A9s" may be replaced with a "ratio Tzt/Tzs."

In the following description, the ignition delay period ID, the compression end temperature Tcomp, the exhaust gas pressure Pe, the exhaust gas temperature Te, the intake gas temperature Ti, and the temperature Tz will be collectively referred to as an "ignition delay period correlated value." Furthermore, the "ratio A4t/A4s based on the ignition delay period ID" in the above-mentioned Eq. (24), the "ratio A5t/A5s based on the compression end temperature Tcomp" in the above-mentioned Eq. (26), the "ratio A6t/A6s based on the exhaust gas pressure Pe" in the above-mentioned Eq. (28), the "ratio A7t/A7s based on the exhaust gas temperature Te" in the above-mentioned Eq. (30), the "ratio A8t/A8s based on the intake gas temperature Ti" in the above-mentioned Eq. (32), and the "ratio A9t/A9s based on the temperature Tz" in the above-mentioned Eq. (35) will be collectively referred to as a ratio "A10t/A10s based on the ignition delay period correlated value."

This "A10t/A10s" represents the degree of deviation of the soot discharge amount (instantaneous value) from the steady discharge amount attributable to the "deviation of the transient value from the steady value regarding the ignition delay period correlated value" in the transient operation state. Through use of this "A10t/A10s," the above-described Eqs. (24), (26), (28), (30), (32), and (35) can be collectively represented by the following Eq. (37).

$$\text{Transient correction value} = \frac{A1t}{A1s} \cdot \frac{A2t}{A2s} \cdot \frac{A10t}{A10s} \cdot \frac{B1s}{B1t} \cdot \frac{B2t}{B2s} \tag{37}$$

In the following, an additional explanation is provided for the case where the "ratio A10t/A10s based on the ignition delay period correlated value" is contained in the generation correction term (that is, the case where the correction based on the ignition delay period correlated value is performed) as shown in the above-described Eq. (37). In this case, as described above, the transient correction value may be calculated while the correction based on the ignition delay period correlated value is always performed (see Eq. (37)). Alternatively, the transient correction value may be calculated in accordance with Eq. (37), in which the correction based on the ignition delay period correlated value is taken into consideration, only when a predetermined condition is satisfied, and calculated in accordance with the following Eq. (38) (which is an equation obtained by removing the term "A10t/A10s" from Eq. (37)), in which the correction based on the ignition delay period correlated value is not taken into consideration, when the predetermined condition is not satisfied. In the following, an example of processing for various cases in which the transient correction value is calculated in consideration of the correction based on the ignition delay period correlated value only when the predetermined condition is satisfied will be described with reference to FIGS. 33 to 36.

$$\text{Transient correction value} = \frac{A1t}{A1s} \cdot \frac{A2t}{A2s} \cdot \frac{B1s}{B1t} \cdot \frac{B2t}{B2s} \quad (38)$$

First, an example shown in FIG. 33 will be described. In this example, first, in step 3305, a determination is made as to whether or not an in-cylinder oxygen concentration CORRELATED VALUE is smaller than a predetermined value. Here, the above-mentioned intake gas oxygen concentration, oxygen concentration of the in-cylinder gas, oxygen concentration of the exhaust gas, excess air ratio of the in-cylinder gas, etc. can be used as the in-cylinder oxygen concentration CORRELATED VALUE.

When a "Yes" determination is made in step 3305, in step 3310, a determination is made as to whether or not the transient value of the ignition delay period correlated value has deviated from the steady value thereof in such a direction that the soot discharge amount increases. Here, the "case where the transient value of the ignition delay period correlated value has deviated from the steady value thereof in such a direction that the soot discharge amount increases" corresponds to the case where the "transient value IDt of the ignition delay period ID is smaller than the steady value IDs" when the ignition delay period ID is used as the ignition delay period correlated value, and corresponds to the case where the "transient value Pet of the exhaust gas pressure Pe is larger than the steady value Pes" when the exhaust gas pressure Pe is used as the ignition delay period correlated value.

In the case where a "Yes" determination is made in both steps 3305 and 3310, the transient correction value is calculated by use of Eq. (37) in step 3315. That is, the soot discharge amount is estimated in consideration of the correction based on the ignition delay period correlated value. Meanwhile, in the case where a "No" determination is made in step 3305 or 3310, the transient correction value is calculated by use of Eq. (38) in step 3320. That is, the soot discharge amount is estimated without consideration of the correction based on the ignition delay period correlated value.

As described above, in the example shown in FIG. 33, the soot discharge amount is estimated without consideration of the correction based on the ignition delay period correlated value when the in-cylinder oxygen concentration CORRELATED VALUE is equal to or greater than a predetermined value. This is based on the fact that, when the in-cylinder oxygen concentration is high, soot is less likely to be produced, and the degree of influence of the length of the ignition delay period ID on the degree of generation of soot is small. With this operation, when the soot discharge amount is calculated, it becomes possible to avoid an increase in calculation load, which would otherwise occur when the ignition delay period is taken into consideration (that is, the ratio "A10t/A10s" is added to the generation correction term), without lowering calculation accuracy, in the case where the in-cylinder oxygen concentration is high.

Figure 33:
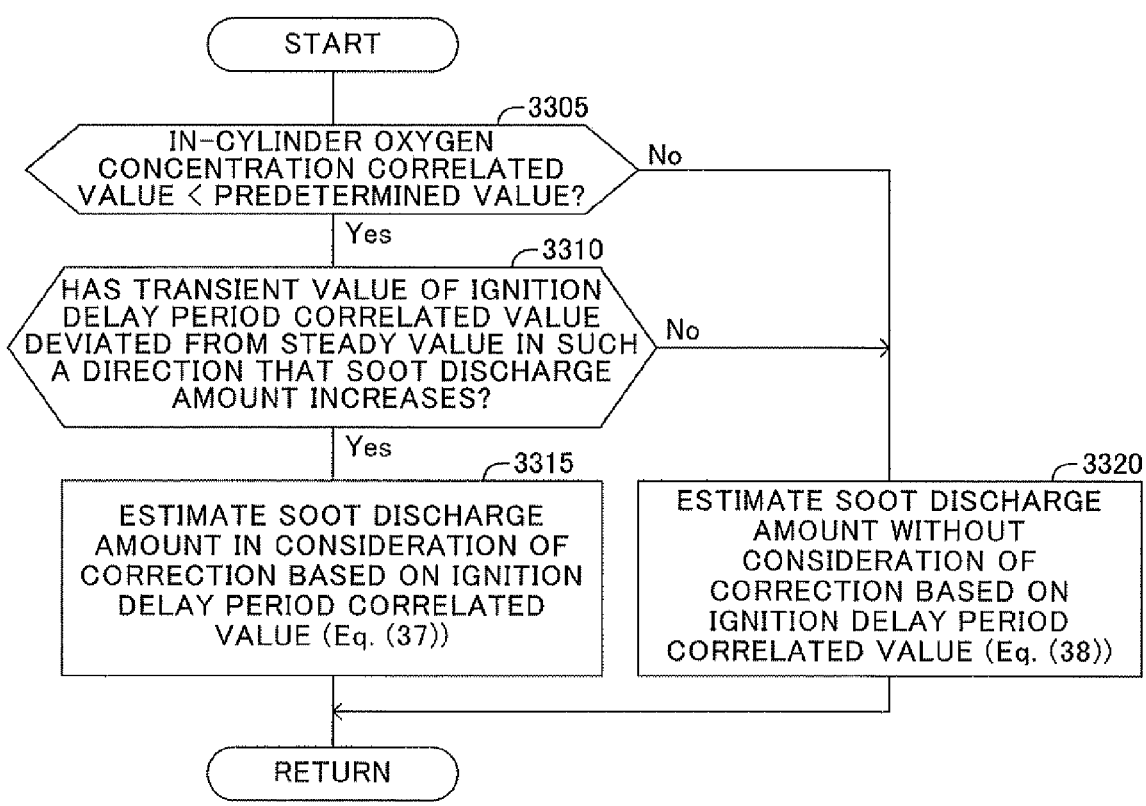
FIG. 33 is a flowchart showing an example of processing for the case where the soot discharge amount is estimated in consideration of correction based on an ignition delay period correlated value only under a predetermined condition.

In addition, in the example shown in FIG. 33, when the "transient value of the ignition delay period correlated value has not deviated from the steady value thereof in such a direction that the soot discharge amount increases," the soot discharge amount is estimated without consideration of correction based on the ignition delay period correlated value. With this operation, the soot discharge amount is calculated without consideration of the ignition delay period in the case where the "transient value of the ignition delay period correlated value has deviated from the steady value thereof in such a direction that the soot discharge amount decreases," which does not raise a problem associated with the soot discharge amount. Accordingly, in such a case, when the soot discharge amount is calculated, it becomes possible to avoid an increase in calculation load, which would otherwise occur when the ignition delay period is taken into consideration (that is, the ratio "A10t/A10s" is added to the generation correction term).

Figure 34:
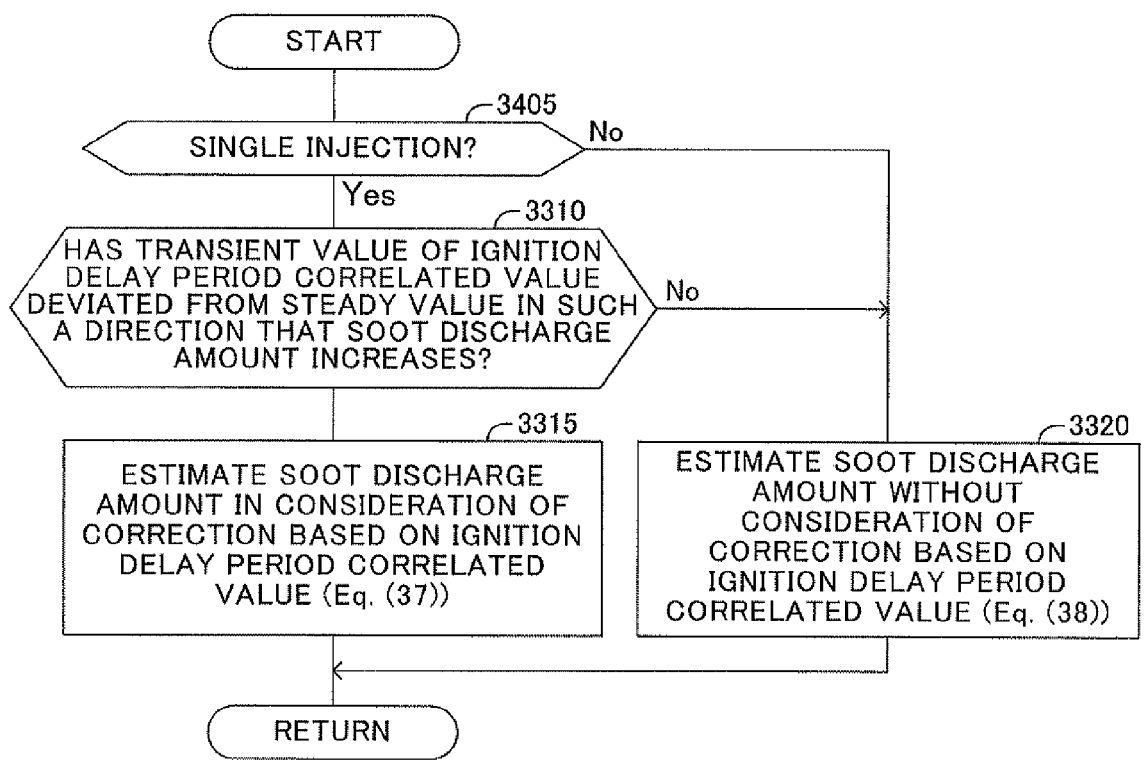
FIG. 34 is a flowchart showing another example of processing for the case where the soot discharge amount is estimated in consideration of correction based on an ignition delay period correlated value only under a predetermined condition.

Next, an example shown in FIG. 34 will be described. This example differs from the example shown in FIG. 33 only in that the above-described step 3305 of the example of FIG. 33 is replaced with step 3405. In step 3405, a determination is made as to whether or not pilot injection is not performed prior to main injection (single injection). That is, in the case where pilot injection is performed prior to main injection, the soot discharge amount is estimated without consideration of correction based on the ignition delay period correlated value. This is based on the fact that, when pilot injection is performed prior to main injection, the compression end temperature becomes stable irrespective of the pressure of exhaust gas, and, therefore, the ignition delay period readily becomes stable. With this operation, in the case where pilot injection is performed prior to main injection, when the soot discharge amount is calculated, it becomes possible to avoid an increase in calculation load, which would otherwise occur when the ignition delay period is taken into consideration (that is, the ratio "A10t/A10s" is added to the generation correction term).

Figure 35:
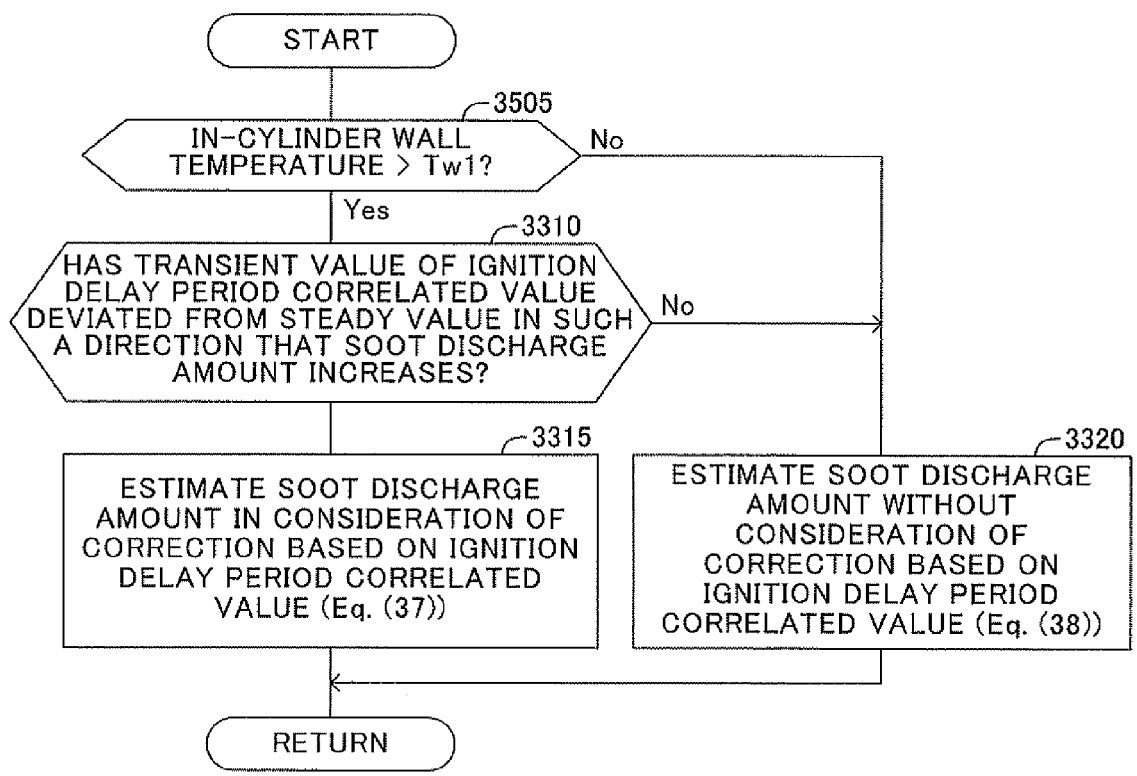
FIG. 35 is a flowchart showing another example of processing for the case where the soot discharge amount is estimated in consideration of correction based on an ignition delay period correlated value only under a predetermined condition.

Next, an example shown in FIG. 35 will be described. This example differs from the example shown in FIG. 33 only in that the above-described step 3305 of the example of FIG. 33 is replaced with step 3505. In step 3505, a determination is made as to whether or not the temperature of the wall (inner wall) of the combustion chamber is higher than a predetermined value Tw1. That is, when the in-cylinder wall temperature is equal to or lower than Tw1, the soot discharge amount is estimated without consideration of correction based on the ignition delay period correlated value. This is based on the fact that, when the in-cylinder wall temperature is low, the compression end temperature hardly increases even when the exhaust gas pressure or the like increases, so that the compression end temperature becomes stable, and, therefore, the ignition delay period readily becomes stable. With this operation, in the case where the in-cylinder wall temperature is low, when the soot discharge amount is calculated, it becomes possible to avoid an increase in calculation load without lowering calculation accuracy, which increase would otherwise occur when the ignition delay period is taken into consideration (that is, the ratio "A10t/A10s" is added to the generation correction term).

Figure 36:
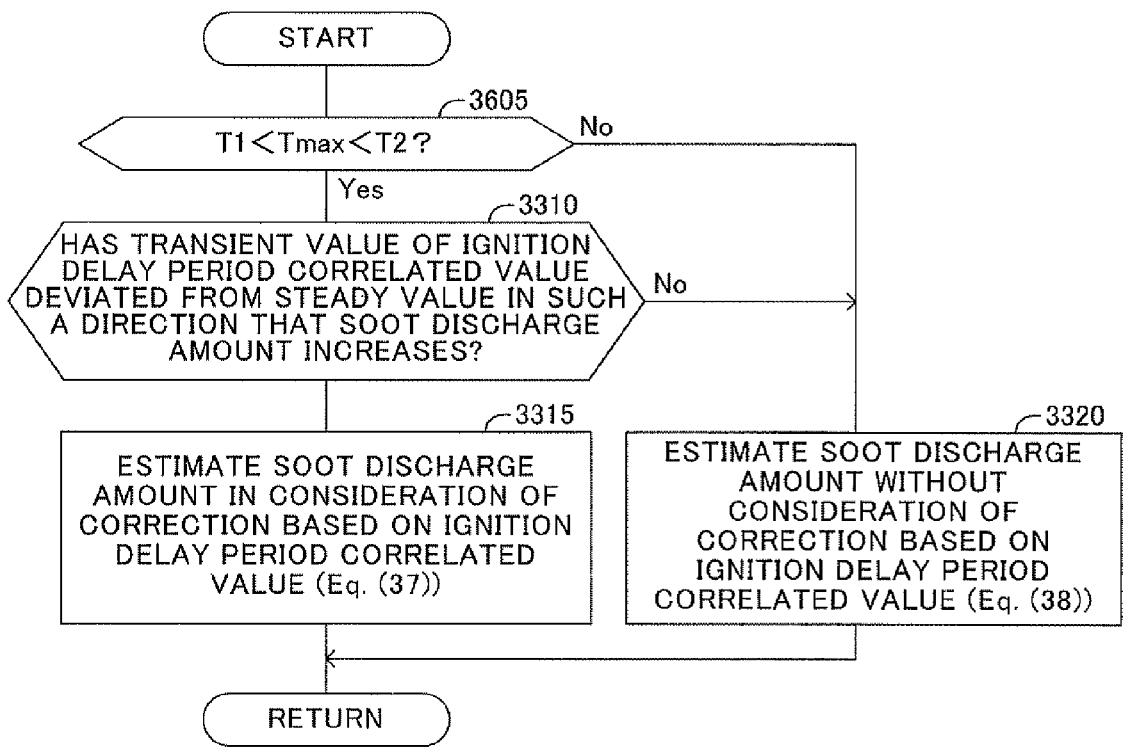
FIG. 36 is a flowchart showing another example of processing for the case where the soot discharge amount is estimated in consideration of correction based on an ignition delay period correlated value only under a predetermined condition.
Figure 37:
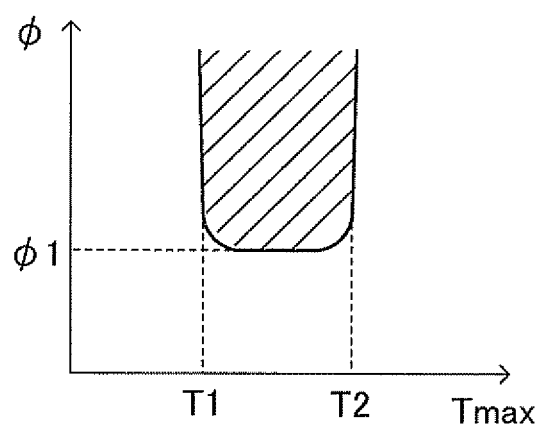
FIG. 37 is a graph showing the relation between equivalence ratio of mist and the maximum flame temperature required for generation of soot.

Next, an example shown in FIG. 36 will be described. This example differs from the example shown in FIG. 36 only in that the above-described step 3305 of the example of FIG. 33 is replaced with step 3605. In step 3605, a determination is made as to whether or not the above-mentioned (maximum) flame temperature Tmax falls within a predetermined range (between T1 and T2). That is, when the flame temperature Tmax falls outside the predetermined range (not higher than T1 or not lower than T2), the soot discharge amount is estimated without consideration of correction based on the ignition delay period correlated value. This is based on the fact that, when the flame temperature Tmax falls outside the predetermined range as shown in FIG. 37, the conditions deviate from a region where soot is readily produced (a hatched region) (that is, soot is less likely to be produced), and the degree of influence of the length of the ignition delay period on the degree of generation of soot is small. With this operation, in the case where the flame temperature Tmax falls outside the predetermined range, when the soot discharge amount is calculated, it becomes possible to avoid an increase in calculation load without lowering calculation accuracy, which increase would otherwise occur when the ignition delay period is taken into consideration (that is, the ratio "A10t/A10s" is added to the generation correction term). Notably, in FIG. 37, φ represents the (average) equivalence ratio of fuel mist. Specifically, for example, T1 and T2 are 1600K and 2200K, respectively, and φ1 is 2. In the above, there has been described various cases in which the transient correction value is calculated in consideration of correction based on the ignition delay period correlated value only when the predetermined condition is satisfied.

The above-described various equations for calculating the transient correction value may be modified through omission of a portion (arbitrary one or more terms) of a plurality of terms contained in each equation.

The invention claimed is:

1. A soot discharge estimating device for an internal combustion engine comprising:
   a steady discharge amount acquisition unit that acquires a steady discharge amount of soot, the steady discharge amount of soot being obtained from a first table in view of current values of an operation speed and a fuel injection amount, the first table showing a relationship between a discharge amount of soot discharged from the internal combustion engine and the operation speed and the fuel injection amount of the internal combustion engine where the internal combustion engine is in a steady operation state;
   a steady value acquisition unit that acquires a steady value of a factor that affects a soot generation speed as a result of reaction of fuel, the steady value of the factor being obtained from a second table in view of a current value of a predetermined parameter, the predetermined parameter representing an operation state of the internal combustion engine, the second table showing a relationship between the predetermined parameter and the factor where the internal combustion engine is in the steady operation state;
   a transient value acquisition unit that acquires a transient value of the factor, the transient value of the factor being a current value of the factor;
   a transient correction value calculation unit that calculates a transient correction value regarding the discharge amount of soot based on a steady characteristic value and a transient characteristic value, the steady characteristic value being obtained on a basis of the steady value of the factor and a predetermined characteristic of the discharge amount of the soot that represents a change in the discharge amount of soot with respect to the value of the factor, and the transient characteristic value being obtained on a basis of the transient value of the factor and the predetermined characteristic of the discharge amount of the soot; and
   a soot discharge amount estimation unit that estimates the discharge amount of soot on a basis of the steady discharge amount and the transient correction value,
   wherein:
   an ignition delay period, which is a period between a point in time at which fuel injection starts and a point in time at which ignition of injected fuel starts, or a value correlated with the ignition delay period is used as the factor that affects the soot generation speed,
   when oxygen concentration of gas within a combustion chamber of the internal combustion engine or a value correlated with the oxygen concentration is less than a predetermined value, the transient correction value calculation unit calculates the transient correction value in consideration of the ignition delay period, which serves as the factor that affects the soot generation speed, or the value correlated with the ignition delay period, and,
   when the oxygen concentration or the value correlated with the oxygen concentration is equal to or greater than the predetermined value, the transient correction value calculation unit calculates the transient correction value without consideration of the ignition delay period, which serves as the factor that affects the soot generation speed, or the value correlated with the ignition delay period.

2. The soot discharge estimating device for an internal combustion engine according to claim 1, wherein
   when pilot injection is not performed prior to main injection, the transient correction value calculation unit calculates the transient correction value in consideration of the ignition delay period, which serves as the factor that affects the soot generation speed, or the value correlated with the ignition delay period, and, when the pilot injection is performed prior to the main injection, the transient correction value calculation unit calculates the transient correction value without consideration of the ignition delay period, which serves as the factor that affects the soot generation speed, or the value correlated with the ignition delay period.

3. The soot discharge estimating device for an internal combustion engine according to claim 1, wherein
   when temperature of a wall of a combustion chamber of the internal combustion engine is greater than a predetermined value, the transient correction value calculation unit calculates the transient correction value in consideration of the ignition delay period, which serves as the factor that affects the soot generation speed, or the value correlated with the ignition delay period, and, when the temperature of the wall of the combustion chamber is equal to or less than the predetermined value, the transient correction value calculation unit calculates the transient correction value without consideration of the ignition delay period, which serves as the factor that affects the soot generation speed, or the value correlated with the ignition delay period.

4. The soot discharge estimating device for an internal combustion engine according to claim 1, wherein
when flame temperature within a combustion chamber of the internal combustion engine in an expansion stroke falls within a predetermined range, the transient correction value calculation unit calculates the transient correction value in consideration of the ignition delay period, which serves as the factor that affects the soot generation speed, or the value correlated with the ignition delay period, and, when the flame temperature falls outside the predetermined range, the transient correction value calculation unit calculates the transient correction value without consideration of the ignition delay period, which serves as the factor that affects the soot generation speed, or the value correlated with the ignition delay period.

5. The soot discharge estimating device for an internal combustion engine according to claim 1, wherein
when a transient value of the ignition delay period, which serves as the factor that affects the soot generation speed, or the value correlated with the ignition delay period, has deviated from a steady value thereof in such a direction that the discharge amount of soot increases, the transient correction value calculation unit calculates the transient correction value in consideration of the ignition delay period or the value correlated with the ignition delay period, and, when the transient value of the ignition delay period or the value correlated with the ignition delay period has not deviated from the steady value in such a direction that the discharge amount of soot increases, the transient correction value calculation unit calculates the transient correction value without consideration of the ignition delay period or the value correlated with the ignition delay period.

6. The soot discharge estimating device for an internal combustion engine according to claim 1, wherein
the transient correction value calculation unit is configured to calculate a ratio between the degree of oxidation of soot in the first half of combustion and that in the second half of combustion on the basis of at least one of the temperature, pressure, and oxygen concentration of gas within the combustion chamber, and calculate the transient correction value in consideration of the ratio.

7. A soot discharge estimating device for an internal combustion engine according to claim 1, wherein the factor that affects the soot oxidation speed is net oxygen concentration of gas within the combustion chamber of the internal combustion engine that contributes to oxidation of soot, the net oxygen concentration being obtained in consideration of a combustion gas intake ratio, which is a ratio of an amount of gas within the combustion chamber required for complete combustion of all fuel of a fuel injection amount to the entire amount of gas within the combustion chamber.

8. A soot discharge estimating device for an internal combustion engine according to claim 1, wherein the factor that affects the soot oxidation speed is a mist overlapping degree, which is a ratio of an amount of gas within the combustion chamber of the internal combustion engine required for complete combustion of all fuel of a fuel injection amount, to an amount of gas within the combustion chamber, excluding a portion of the gas that does not contribute to combustion of the fuel.

* * * * *